(12) United States Patent
Zhou

(10) Patent No.: US 11,241,227 B2
(45) Date of Patent: Feb. 8, 2022

(54) LEAD PUNCTURE NEEDLE

(71) Applicant: Xing Zhou, Guangdong (CN)

(72) Inventor: Xing Zhou, Guangdong (CN)

( * ) Notice: Subject to any disclaimer, the term of this patent is extended or adjusted under 35 U.S.C. 154(b) by 316 days.

(21) Appl. No.: 16/609,980

(22) PCT Filed: Aug. 26, 2017

(86) PCT No.: PCT/CN2017/099205
§ 371 (c)(1),
(2) Date: Oct. 31, 2019

(87) PCT Pub. No.: WO2019/019242
PCT Pub. Date: Jan. 31, 2019

(65) Prior Publication Data
US 2020/0054319 A1  Feb. 20, 2020

(30) Foreign Application Priority Data

Jul. 25, 2017  (CN) .......................... 201710614570.3
Jul. 25, 2017  (CN) .......................... 201720912484.6

(51) Int. Cl.
*A61B 17/06* (2006.01)

(52) U.S. Cl.
CPC .. *A61B 17/06066* (2013.01); *A61B 17/06004* (2013.01); *A61B 2017/061* (2013.01);
(Continued)

(58) Field of Classification Search
CPC ............ A61B 17/0482; A61B 17/0483; A61B 17/0485; A61B 17/06; A61B 17/06004;
(Continued)

(56) References Cited

U.S. PATENT DOCUMENTS 5,364,410 A * 11/1994 Failla ................. A61B 17/0469
606/135
5,817,111 A  10/1998 Riza
(Continued)

FOREIGN PATENT DOCUMENTS

CN  101721235 A  6/2010
CN  203089250 U  7/2013
(Continued)

OTHER PUBLICATIONS

Zhou, Xing, International Search Report, PCT/CN2017/099205, dated Apr. 26, 2018, 4 pgs.
(Continued)

*Primary Examiner* — Melanie R Tyson
(74) *Attorney, Agent, or Firm* — Morgan, Lewis & Bockius LLP

(57) ABSTRACT

A lead puncture needle includes a core rod, a puncture needle, a lead mechanism and a handle. A front end of the core rod includes a blunt head and a lead slot. During puncture, the puncture needle is exposed. After the puncture, the blunt head protrudes out of the puncture needle to avoid injury to normal tissue. When a button is pressed, the core rod moves downward, and the lead slot protrudes from the puncture needle. When the button is pressed again, the core rod moves upward, and the lead slot is retracted into the puncture needle to form traction on a surgical suture. The design of the blunt head ensures that it is retracted during puncture to expose the puncture needle to facilitate puncture and the blunt head is controlled to be exposed outside the puncture needle in a separation process, thereby avoiding accidental injury to the surrounding tissue.

20 Claims, 14 Drawing Sheets

(52) U.S. Cl.
CPC ............... *A61B 2017/06042* (2013.01); *A61B 2017/06085* (2013.01)

(58) Field of Classification Search
CPC .... A61B 17/06066; A61B 2017/06009; A61B 2017/06014; A61B 2017/06042; A61B 2017/06085; A61B 2017/061
See application file for complete search history.

(56) References Cited

U.S. PATENT DOCUMENTS

| | | |
|---|---|---|
| 9,017,361 B2 | 4/2015 | Karabey et al. |
| 2010/0191260 A1 | 7/2010 | Mohajer |
| 2015/0157317 A1 | 6/2015 | Bagaoisan et al. |

FOREIGN PATENT DOCUMENTS

| | | |
|---|---|---|
| CN | 103610479 A | 3/2014 |
| CN | 206197988 U | 5/2017 |
| HK | 1210569 A2 | 4/2016 |
| WO | WO2016/039035 A1 | 3/2016 |

OTHER PUBLICATIONS

Zhou, Xing, Extended European Search Report, EP17918844.6, dated Dec. 4, 2020, 7 pgs.

* cited by examiner

FIG. 6          FIG. 6-1

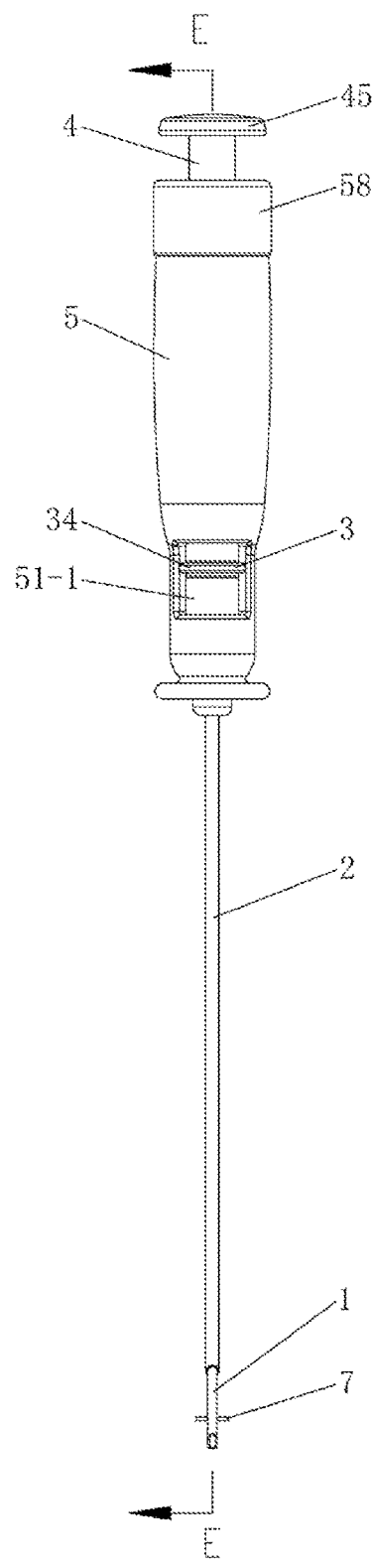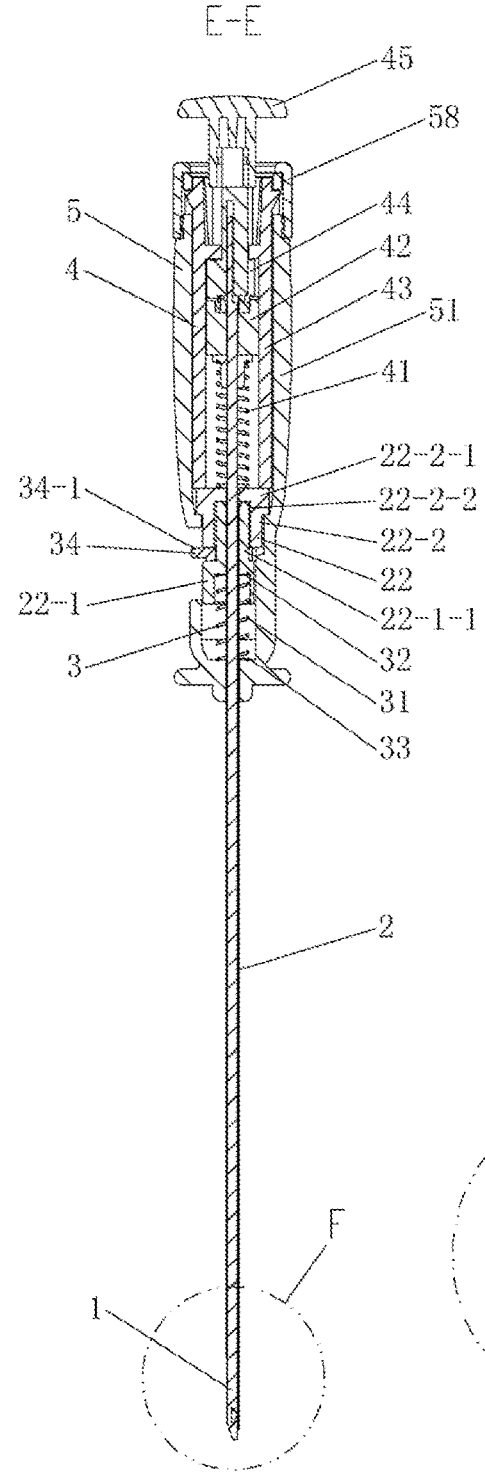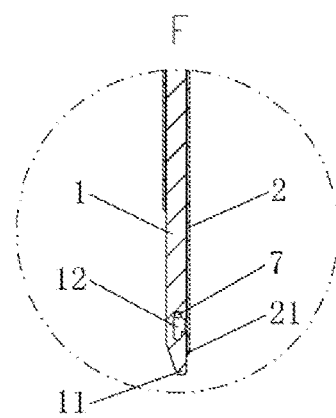
FIG. 7
FIG. 7-1
FIG. 7-2

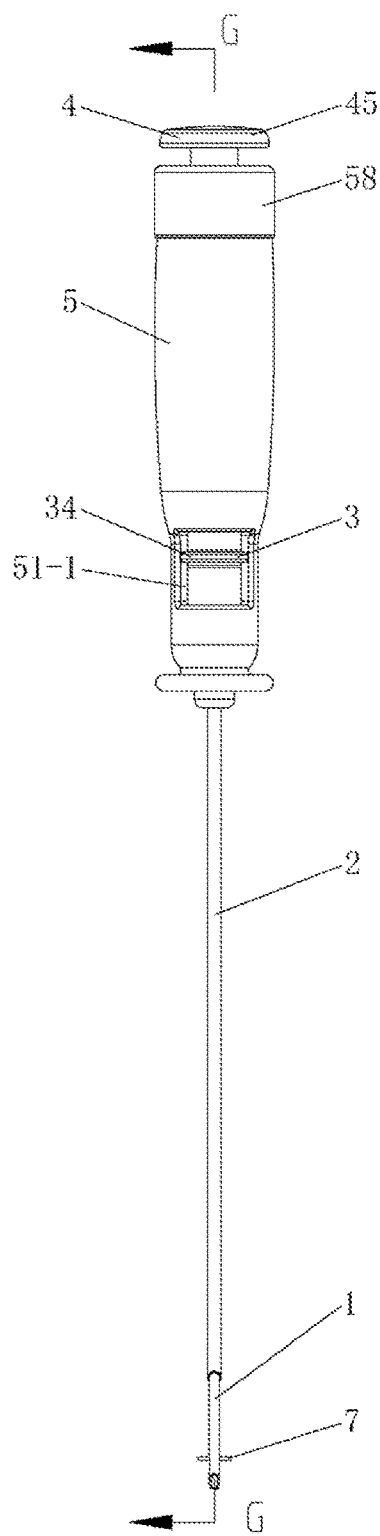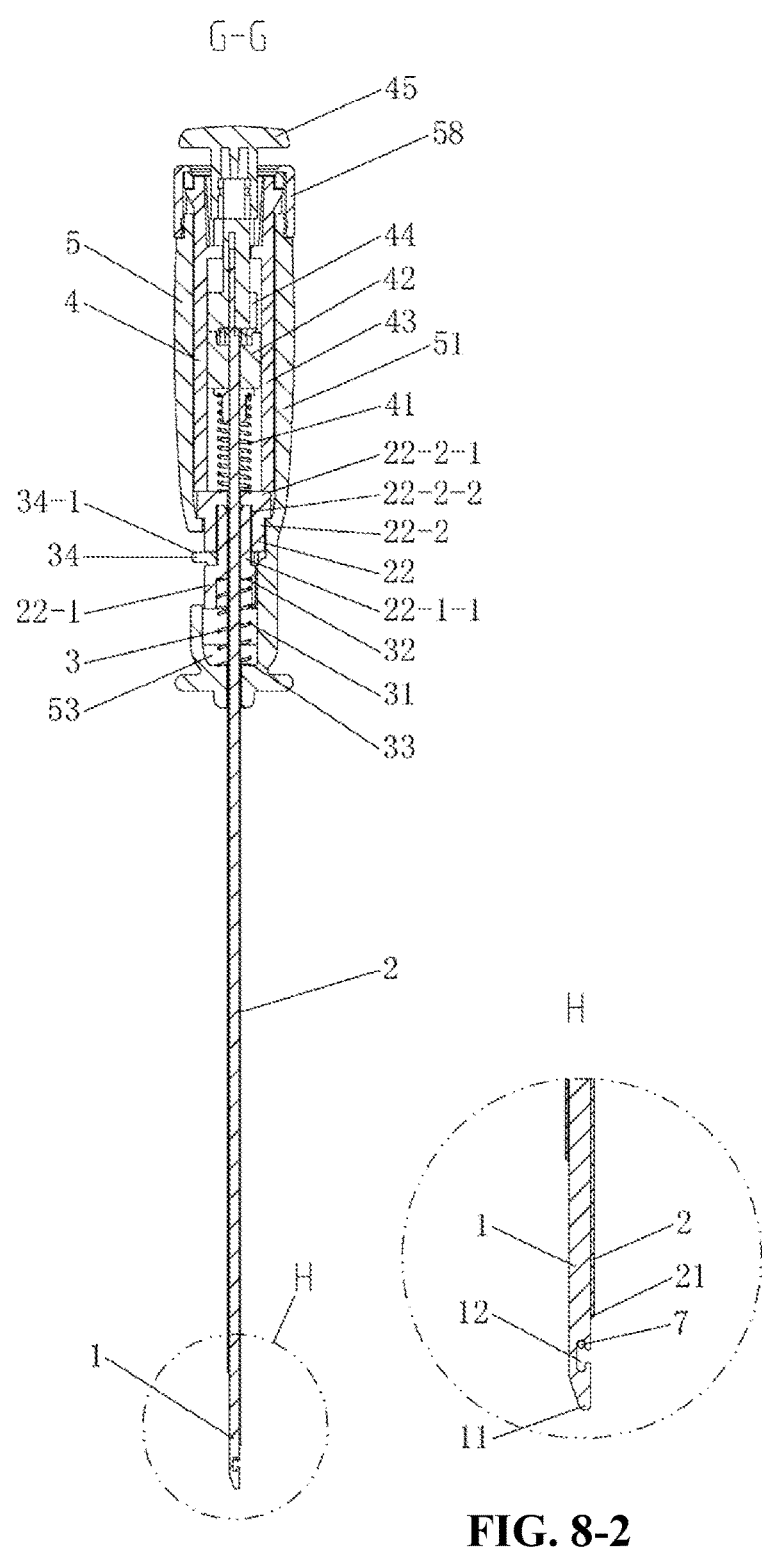
FIG. 8   FIG. 8-1   FIG. 8-2

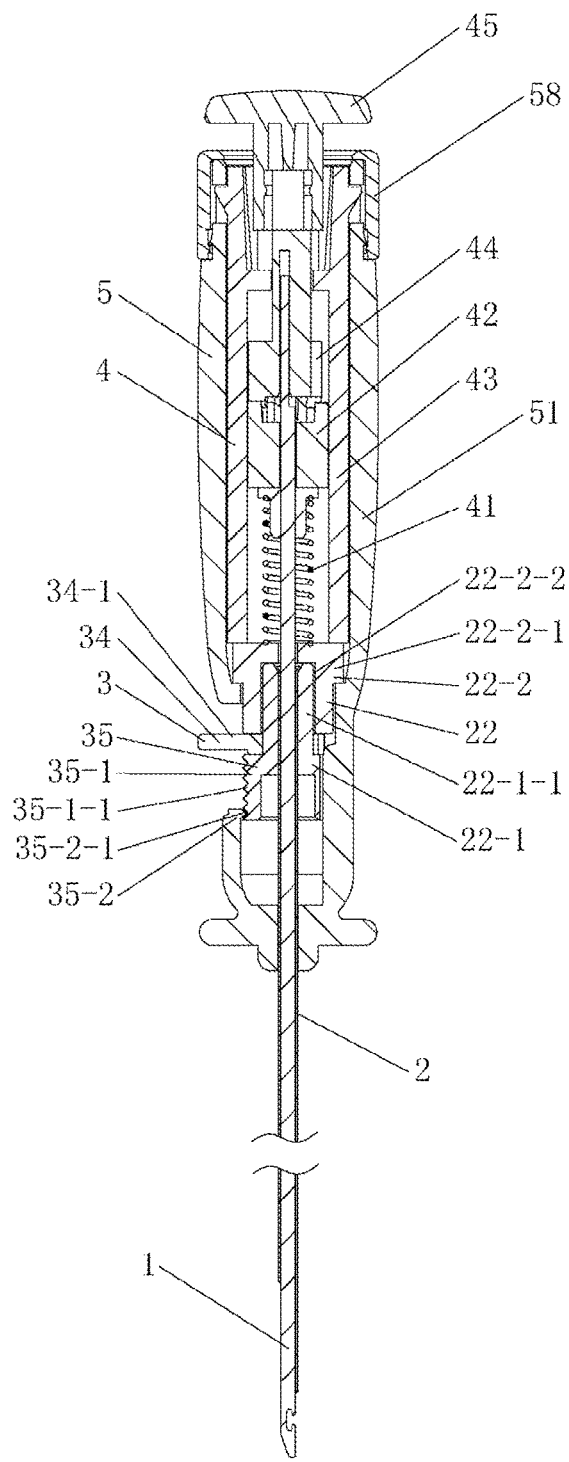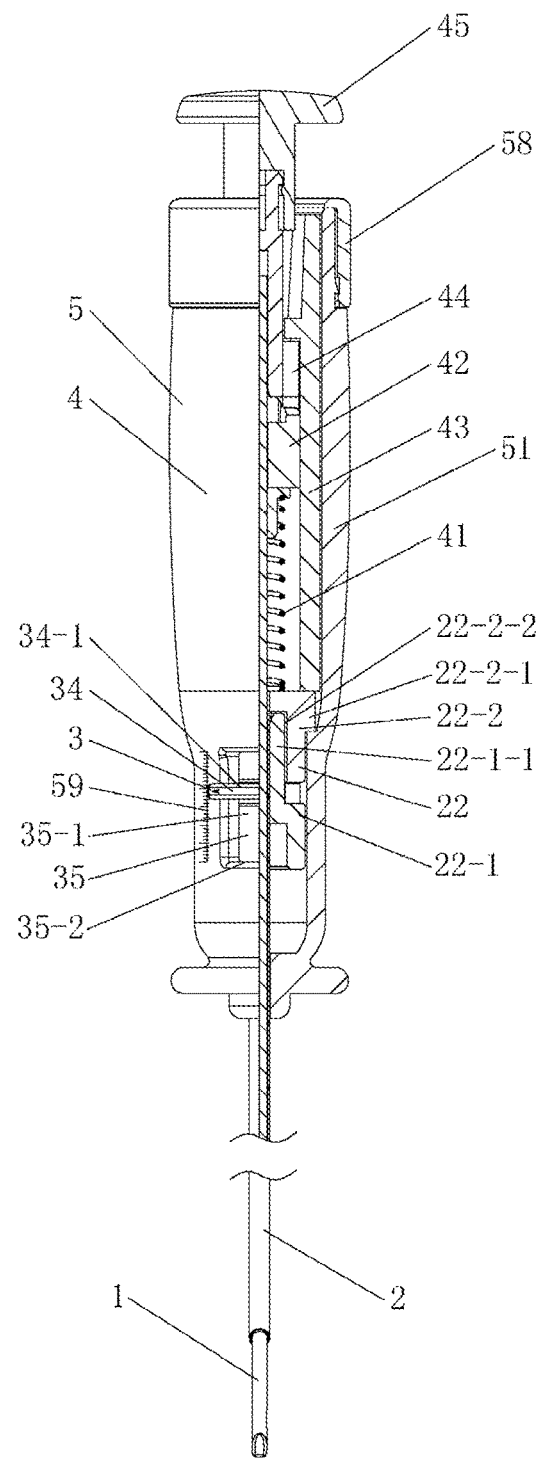
FIG. 10  FIG. 11

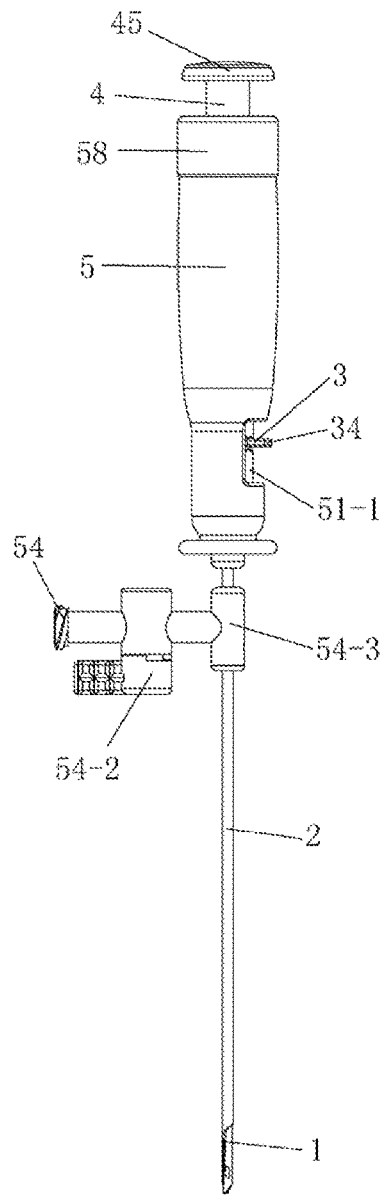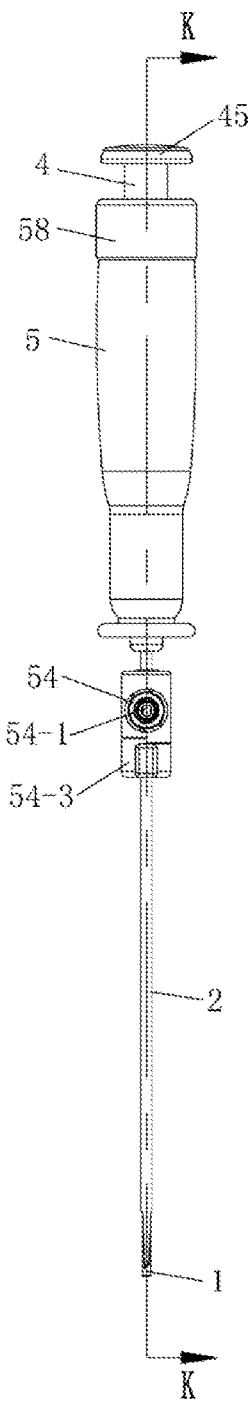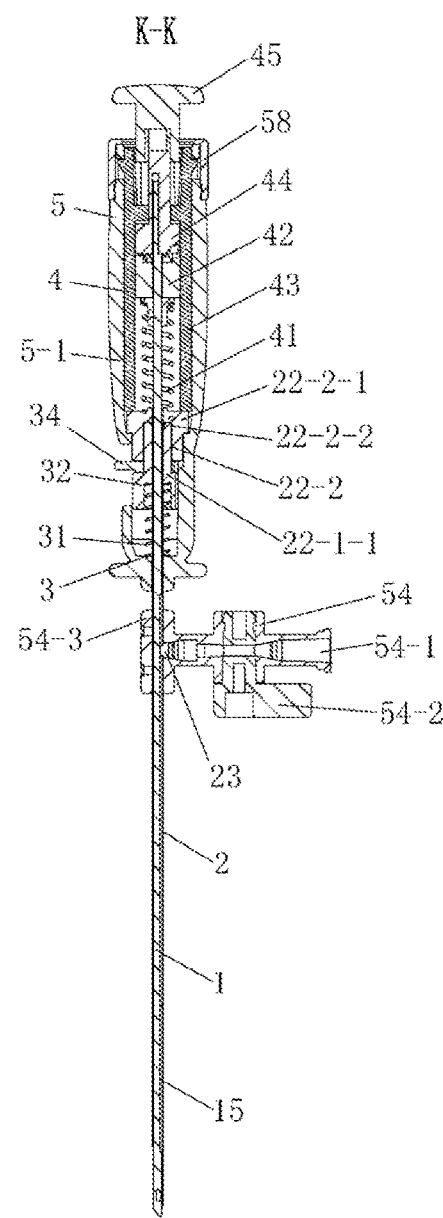
FIG. 13
FIG. 14-1
FIG. 14

LEAD PUNCTURE NEEDLE

CROSS REFERENCE TO RELATED APPLICATIONS

This Application is a United States National Stage Application filed under 35 U.S.C. § 371 of PCT Patent Application Serial No. PCT/CN2017/099205 filed on Aug. 26, 2017, which claims the benefit of and priority to Chinese Patent Application No. 201710614570.3 filed on Jul. 25, 2017, and Chinese Patent Application No. 201720912484.6 filed on Jul. 25, 2017, which are hereby incorporated by reference in their entirety.

FIELD OF THE INVENTION

The present application relates to a surgical operating instrument, and more particularly to a lead puncture needle for use in hernia repair surgery.

BACKGROUND OF THE INVENTION

Hernia is a disease in which an organ or tissue in a human body leaves its normal anatomical position and enters another site through a weak point, defect or pore formed congenitally or postnatally. Both adults and children may suffer from the disease, and it is especially the most common disease in pediatric urology surgery. A preferred treatment method for children in the age of one year or longer and adults is surgery. A usual procedure of surgery is to ligature or repair a defect or weakness. Especially for pediatric patients, the current preferred treatment method is high ligation surgery.

With the popularity of endoscopic surgery, the current hernia surgery is generally performed under an endoscope. At present, a commonly used method is to make an incision in skin first, then use a suture needle or a hernia ring needle with a suture to extraperitoneally undermine and separate along an inner semi-circumference of an internal ring to puncture into peritoneum, withdraw the suture needle or the hernia ring needle, then use the suture needle or the hernia ring needle with a suture to extraperitoneally undermine via the same opening and separate along an outer semi-circumference of the internal ring to puncture into the peritoneum, withdraw the suture needle or the hernia ring needle, and pull back the suture to a needle insertion part with a hooked needle to lead the suture out of the body and knot. The processes of puncture, separation for suture leading, and returning back during surgery require different instruments. The surgical procedure is very cumbersome, and the sharp tip of the suture needle or the hernia ring needle may easily cause accidental injury to the surrounding tissue and blood vessels in an undermining and separating process. Therefore, it is necessary to improve the surgical instruments in the current hernia surgery.

SUMMARY

A lead puncture needle of the present application includes a core rod 1, a puncture needle 2, a puncture safety protection mechanism 3, a lead mechanism 4 and a handle 5, where A. a front end of the core rod 1 includes a blunt head 11 and a lead slot 12, and the lead slot 12 is arrange on the blunt head 11;

B. the puncture needle 2 is a hollow needle, and a sharp tip 21 is arranged at a front end of the puncture needle; and the core rod 1 is movably mounted in the puncture needle 2;

C. the lead mechanism 4 includes a leading spring 41, a rotary positioning block 42, a stroke control member 43, a linear push block 44, and a button 45; the stroke control member 43 is a tubular structure, a tube wall thereof is provided with a stroke control convex step 43-1, and the stroke control member 43 is movably mounted in a mounting slot 52 of a shell 51 of the handle 5; the leading spring 41 is arranged at a front end of the rotary positioning block 42; the rotary positioning block 42 is provided with a central hole 42-1, a groove 42-2 and a convex step 42-3; a rear end of the core rod 1 passes through the central hole 42-1 of the rotary positioning block 42, and the rotary positioning block 42 may rotate around the core rod 1; when the button 45 is pressed, the convex step 42-3 pushes under the stroke control convex step 43-1, the core rod 1 moves downward, and the leading spring (41) is compressed, so that the lead slot 12 capable of hooking a surgical suture protrudes from the sharp tip 21 of the puncture needle 2; when the button 45 is pressed again, a rotary driving block 44-1 on the linear push block 44 pushes the rotary positioning block 42 to rotate, the stroke control convex step 43-1 slides into the groove 42-2, the core rod 1 moves upward under an elastic force of the leading spring 41, and the lead slot 12 is retracted into the sharp tip 21 of the puncture needle 2 to prevent the surgical suture from slipping off and form traction on the surgical suture; and D. the handle 5 includes the shell 51 and the mounting slot 52; and the core rod 1, the puncture needle 2, the puncture safety protection mechanism 3, and the lead mechanism 4 are mounted in the mounting slot 52 of the shell 51.

Further, the rear end of the core rod 1 is provided with a positioning stopper 13 and a rotation preventing convex step 14 for preventing rotation of the core rod 1.

The positioning stopper 13 of the core rod 1 is arranged at a bottom of the rotary positioning block 42, and after the rear end of the core rod 1 passes through the central hole 42-1 of the rotary positioning block 42, the rotation preventing convex step 14 of the core rod 1 is embedded in the positioning hole 44-3 on the linear push block 44.

The core rod 1 or/and the puncture needle 2 has/have special geometric shapes conforming to clinical requirements, at least including a linear shape, an arc shape, an L shape, a C shape, a U shape, an S shape, and the like. Because in a surgical procedure, the surgical suture needs to undermine along an outer circumference of an internal ring and separate to a back side of the internal ring, the core rod 1 or the puncture needle 2 is designed into an arc shape or the like in accordance with the clinical requirements to facilitate the surgical procedure.

The lead slot 12 is a bidirectional lead slot that may pull the surgical suture into tissue or pull the surgical suture out of the tissue. When the core rod 1 moves forward, a surgical suture 7 is placed at a rear end of the lead slot 12. When the core rod 1 moves backward, the surgical suture 7 is placed at a front end of the lead slot 12. The lead slot 12 may realize leading when the core rod 1 advances or retreats in two directions.

The puncture needle 2 includes a mounting convex step 22, and a puncture needle mounting slot 53 is arranged on the shell 51. The puncture needle 2 is mounted in the puncture needle mounting slot 53 on the shell 51 through the mounting convex step 22.

The mounting convex step 22 and the puncture needle mounting slot 53 may be connected together by concave-convex clamp fit, screw connection, interference fit, bonding, or the like.

The lead puncture needle 100 further includes the puncture safety protection mechanism 3. The puncture safety protection mechanism 3 may be an automatic protection mechanism or a manual protection mechanism. The puncture safety protection mechanism 3 may enable the lead puncture needle of the present application to better control a puncture process of the puncture needle 2 in the puncture process, thereby preventing the puncture needle 2 from causing accidental injury of surrounding tissue due to excessively fast puncture speed or excessive puncture depth in the puncture process, and ensuring the puncture needle 2 to be safer to use.

Further, the puncture safety protection mechanism 3 is an automatic protection mechanism.

The puncture safety protection mechanism 3 includes a safety spring 31, a safety spring rear positioning member 32 and a safety spring front positioning member 33. The safety spring 31 is mounted between the safety spring rear positioning member 32 and the safety spring front positioning member 33. When the safety spring 31 is compressed, the sharp tip 21 of the puncture needle 2 is exposed to perform puncture. After the puncture is completed, under an elastic force of the safety spring 31, the blunt head 11 at a far end of the core rod 1 protrudes out of the sharp tip 21 of the puncture needle 2 for protection and avoidance of injury to normal tissue.

Further, the safety spring 31, the safety spring rear positioning member 32 and the safety spring front positioning member 33 are arranged outside the stroke control member 43. When a resistance is present in puncture, the blunt head 11 of the core rod 1 arranged inside the puncture needle 2 moves backwards under the resistance, and the safety spring 31 is compressed, causing the blunt head 11 at the far end of the core rod 1 to retract into the puncture needle 2 such that the sharp tip 21 of the puncture needle 2 is exposed to perform puncture. After the tissue is punctured, the resistance disappears, and under the elastic force of the safety spring 31, the blunt head 11 at the far end of the core rod 1 protrudes out of the sharp tip 21 of the puncture needle 2 for protection and avoidance of injury to normal tissue.

When in use, the surgical suture 7 is threaded into the lead slot 12 of the core rod 1, and then the skin is punctured. At this time, the blunt head 11 of the core rod 1 moves backwards under skin resistance, and the positioning stopper 13 of the core rod 1 pushes the rotary positioning block 42 to drive the stroke control member 43, the linear push block 44 and the handle 45 to move backward together. At this time, the spring front positioning member 33 arranged on the stroke control member 43 moves backward to compress the safety spring 31, causing the blunt head 11 at the far end of the core rod 1 to retract into the puncture needle 2 such that the sharp tip 21 of the puncture needle 2 is exposed to perform puncture. When the puncture is completed, the resistance disappears. At this time, under resilience of the safety spring 31, the spring front positioning member 33 moves forward to drive the stroke control member 43 to restore forward, and drive the linear push block 44 and the handle 45 to restore forward together. The core rod 1 restores to an initial state under restoring force, and the blunt head 11 at the far end of the core rod 1 protrudes out of the sharp tip 21 of the puncture needle 2 for protection again and avoidance of injury to normal tissue.

At this time, the button 45 is pressed to drive the linear push block 44 to move downward. The rotary driving mechanism 44-1 of the linear push block 44 pushes the rotary positioning block 42 to rotate, and the convex step 42-3 pushes under the stroke control convex step 43-1. The core rod 1 moves downward so that the lead slot 12 capable of hooking the surgical suture protrudes from the sharp tip 21 of the puncture needle 2. The button 45 is pressed and held, the lead puncture needle of the present application extraperitoneally undermines along an inner semi-circumference of the internal ring and separates to a rear side of the internal ring to puncture into peritoneum 8, and then the surgical suture 7 is released. It is necessary to ensure that the blunt head 11 of the core rod 1 is exposed to an outer part of the sharp tip 21 of the puncture needle 2 in an undermining and separating process all the time until reaching the peritoneum 8. Under a resistance of the peritoneum 8, the core rod 1 retracts, and the peritoneum 8 is punctured by the sharp tip 21 of the puncture needle 2. Since an end part of the core rod 1 adopts a smooth blunt-head design, accidental injury to surrounding tissue in the undermining and separating process may be well avoided. In particular, accidental injury to important parts such as arteries may be avoided. When reaching the peritoneum 8, since a large puncture force is required for puncturing the peritoneum 8, at this time, the core rod 1 retracts into the puncture needle 2 under a large resistance, and the sharp tip 21 of the puncture needle 2 is used to perform puncture.

After release, the lead puncture needle 100 is retracted to a needle insertion part of the internal ring, and then the button 45 is pressed and held. The lead puncture needle 100 extraperitoneally undermines along an outer semi-circumference of the internal ring and separates to the rear side of the internal ring to puncture into the peritoneum 8. The surgical suture 7 is placed into the lead slot 12 at the front end of the core rod 1 again. The button 45 is pressed, and the rotary driving block 44-1 on the linear push block 44 pushes the rotary positioning block 42 to rotate. The stroke control convex step 43-1 slides into the groove 42-2, and the core rod 1 moves upward under the elastic force of the leading spring 41. The lead slot 12 is retracted into the sharp tip 21 of the puncture needle 2, and the lead puncture needle 100 is retracted backward. The core rod 1 drives the surgical suture 7, and the surgical suture 7 is led out of the body, knotted and fixed.

The spring front positioning member 33 is arranged on the stroke control member 43.

The spring front positioning member 33 may be integrally fabricated on the stroke control member 43. The spring front positioning member 33 is integrally fabricated on the stroke control member 43, and the fabrication and assembly processes are more convenient.

The spring front positioning member 33 is detachably connected to the stroke control member 43. The spring front positioning member 33 may be connected to the stroke control member 43 by screw connection, concave-convex clamp fit connection, interference fit connection, bonding, or the like. Of course, other connection modes may be adopted by those skilled in the art without departing from the scope of protection of the present application.

The safety spring 31, the safety spring rear positioning member 32 and the safety spring front positioning member 33 may also be arranged in the puncture needle mounting slot 53 at a front end of the stroke control member 43. The puncture safety protection mechanism 3 further includes a shift handle 34. When the shift handle 34 is pushed forward, the safety spring 31 is compressed, the puncture needle 2 moves forward, and the sharp tip 21 is exposed to perform puncture. After the puncture is completed, the shift handle 34 is released. Under the elastic force of the safety spring 31, the puncture needle 2 moves backward, and the blunt head 11 at the far end of the core rod 1 protrudes out of the sharp tip 21 of the puncture needle 2 for protection and avoidance of injury to normal tissue.

The shift handle 34 includes a limiting shift button 34-1, the shell 51 of the handle 5 is provided with a shift button movement slot 51-1, and the limiting shift button 34-1 may move back and forth in the shift button movement slot 51-1.

The shift handle 34 may be integrally fabricated on the puncture needle 2 or may be detachably connected to the puncture needle 2.

The shift handle 34 is connected to the puncture needle 2 by screw connection, concave-convex clamp fit connection, interference fit connection, bonding, or the like.

The mounting convex step 22 includes a connecting end 22-1 and a limiting end 22-2. The connecting end 22-1 includes a connecting rod 22-1-1, and the limiting end 22-2 includes a connecting rod mounting hole 22-2-1 and a limiting convex step 22-2-2. The puncture needle mounting slot 53 is provided with a limiting slot 53-1. The connecting rod 22-1-1 may be mounted in the connecting rod mounting hole 22-2-1, and the limiting convex step 22-2-2 of the limiting end 22-2 may be mounted in the limiting slot 53-1, that is, the puncture needle 2 is mounted in the puncture needle mounting slot 53.

The safety spring front positioning member 33 is arranged at a far end of the puncture needle mounting slot 53 of the handle 5. The safety spring rear positioning member 32 is arranged at a near end of the puncture needle mounting slot 53. In an actual fabrication process, a bottom of the puncture needle mounting slot 53 may be directly arranged as the safety spring front positioning member 33, or the safety spring front positioning member 33 may be separately designed and mounted at the far end of the puncture needle mounting slot 53. Similarly, a bottom of the connecting end 22-1 of the puncture needle 2 may be directly arranged as the safety spring rear positioning member 32, or the safety spring rear positioning member 32 may be separately designed and mounted at a near end of the connecting end 22-1 of the puncture needle 2. The safety spring 31 is mounted between the mounting convex step 22 of the puncture needle 2 and the bottom of the puncture needle mounting slot 53 of the handle.

When in use, the surgical suture 7 is threaded into the lead slot 12 of the core rod 1. The shift handle 34 is pushed forward, the safety spring 31 is compressed, the puncture needle 2 moves forward, and the sharp tip 21 is exposed to perform puncture. After the puncture is completed, the shift handle 34 is released. Under the elastic force of the safety spring 31, the puncture needle 2 moves backward, the blunt head 11 at the far end of the core rod 1 protrudes out of the sharp tip 21 of the puncture needle 2 for protection and avoidance of injury to normal tissue. The blunt head 11 is kept in a protruded state, the lead puncture needle of the present application extraperitoneally undermines along the inner semi-circumference of the internal ring and separates to the peritoneum 8 at the rear side of the internal ring, and then the shift handle 34 is pushed forward. The safety spring 31 is compressed, the puncture needle 2 moves forward, and the sharp tip 21 is exposed to puncture the peritoneum 8. After the puncture is completed, the shift handle 34 is released, and the sharp tip 21 of the puncture needle 2 is retracted.

At this time, the button 45 is pressed to drive the linear push block 44 to move downward. The rotary driving mechanism 44-1 of the linear push block 44 pushes the rotary positioning block 42 to rotate, and the convex step 42-3 pushes under the stroke control convex step 43-1. The core rod 1 moves downward so that the lead slot 12 protrudes from the sharp tip 21 of the puncture needle 2, and the surgical suture 7 in the lead slot 12 is released. Then, the button 45 is pressed again, the rotary driving block 44-1 on the linear push block 44 pushes the rotary positioning block 42 to rotate. The stroke control convex step 43-1 slides into the groove 42-2, and the core rod 1 moves upward under the elastic force of the leading spring 41. The lead slot 12 is retracted into the sharp tip 21 of the puncture needle 2, and the lead puncture needle 100 is retracted backward to the needle insertion part of the internal ring.

Then, the lead puncture needle 100 extraperitoneally undermines along the outer semi-circumference of the internal ring and separates to the peritoneum 8 at the rear side of the internal ring. The shift handle 34 is pushed forward, the safety spring 31 is compressed, the puncture needle 2 moves forward, and the sharp tip 21 is exposed to puncture the peritoneum 8. After the puncture is completed, the shift handle 34 is released, and the sharp tip 21 of the puncture needle 2 is retracted. Then, the button 45 is pressed so that the lead slot 12 protrudes from the sharp tip 21 of the puncture needle 2. The surgical suture 7 is placed into the lead slot 12 at the front end of the core rod 1 again. Then, the button 45 is pressed, the lead slot 12 is retracted into the puncture needle 2, and the lead puncture needle 100 is retracted backward, the core rod 1 drives the surgical suture 7, and the surgical suture 7 is led out of the body, knotted and fixed.

The entire surgical procedure is completed by only the lead puncture needle of the present application. The lead puncture needle of the present application has the advantages of being simple and convenient compared with the condition that multiple instruments are needed in a current surgical procedure to complete the surgical procedure. In particular, the design of the retractable smooth blunt head and the safety spring ensures that the sharp puncture needle may be exposed in time to facilitate puncture during puncture, and meanwhile, in the undermining and separation process, the smooth blunt head may be controlled to be exposed outside the puncture needle all the time. Therefore, accidental injury to the surrounding tissue caused by the sharp tip in the undermining and separation process is effectively avoided, and the use process is safer. Moreover, the smooth blunt head may better reduce friction in movement in the undermining process, making the undermining process smoother.

In addition, the puncture safety protection mechanism 3 may also be a manual protection mechanism.

When the puncture safety protection mechanism 3 is a manual protection mechanism, the safety protection mechanism 3 includes a shift handle 34 and a stroke control mechanism 35, and the stroke control mechanism 35 includes a sliding block 35-1 and a limiting block 35-2.

Further, a total stroke of the stroke control mechanism 35 is controlled to be 1 mm-15 mm. The shift handle 34 may drive the stroke control mechanism 35 to move back and forth in the shift button movement slot 51-1. An end part of the shift button movement slot 51-1 and the limiting block 35-2 act together to achieve the purpose of limiting the total movement stroke of the sliding block 35-1. The total stroke control of the stroke control mechanism 35 may prevent the puncture needle 2 from accidentally injuring the surrounding tissue due to excessive puncture depth in the puncture process.

A step length of the sliding block 35-1 is 1 mm-5 mm. The small step length of the sliding block 35-1 is designed so that every time when the shift handle 34 is pushed forward in the puncture process, the distance that the puncture needle 2 advances is controlled within the step length. Therefore, accidental injury to the surrounding tissue due to excessively fast puncture speed or excessive puncture depth is effectively prevented in the puncture process, and the use process is safer.

The stroke control mechanism 35 may be a spiral progressive mechanism, or a linear stepping mechanism, or the like. Of course, those skilled in the art may also design other various structures according to the actual situation without departing from the scope of protection of the present patent application.

In use, when the puncture needs to be performed, the shift handle 34 is pushed forward. The sliding block 35-1 of the stroke control mechanism 35 advances according to a designed step length range to drive the puncture needle 2 to move forward, and the sharp tip 21 of the puncture needle 2 is exposed to perform puncture. When it is necessary to undermine along an outer side of the peritoneum and separate the tissue, the shift handle 34 is retracted backward. The puncture needle 2 is retracted backward under driving of the stroke control mechanism 35, and the sharp tip 21 of the puncture needle 2 is retracted to expose the blunt head of the core rod 1 to realize protection in the undermining and separation process.

Further, the stroke control convex step 43-1 is arranged on an inner wall of the stroke control member 43. By arranging the stroke control convex step 43-1 on the inner wall of the stroke control member 43, space may be effectively saved, frictional resistance during rotation of the rotary positioning block 42 is reduced, and the use process is more convenient.

A limiting convex step 44-2 is arranged on the linear push block 44. The limiting convex step 44-2 cooperates with a limiting groove 43-2 on the stroke control member 43 to effectively prevent the linear push block 44 from being accidentally detached from the stroke control member 43 during use.

The linear push block 44 and the button 45 may be fabricated into a whole.

The linear push block 44 and the button 45 may be connected together by concave-convex clamp fit, screw connection, interference fit, bonding, or the like.

The linear push block 44 and the button 45 may be fabricated into a whole or connected together by various connection modes without departing from the scope of protection of the present application.

The shell 51 is provided with a press block 55 and a sealing member 56. The core rod 1 passes through a central hole 55-1 of the press block 55 and a central hole 56-1 of the sealing member 56. The press block 55 presses the sealing member 56. The sealing member 56 forms dynamic seal for the core rod 1. When surgery under a laparoscope is performed, it is necessary to ensure the stability of pneumoperitoneum. The dynamic seal design may ensure the stability of the pneumoperitoneum well during the surgery and ensure smooth progress of the surgery.

Further, one end of the leading spring 41 is connected to the positioning stopper 13 at the rear end of the core rod 1, and the other end is connected to the press block 55 of the shell 51.

The shell 51 is provided with an air/water inlet 54. Through the air/water inlet 54, air may be injected into an abdominal cavity to form pneumoperitoneum. A liquid, such as normal saline, may also be injected into a surgical site via the puncture needle 2 through the air/water inlet 54. Under the action of the normal saline, a slight local separation is formed at a junction of the peritoneum and an abdominal wall, thereby facilitating the undermining and separation of the blunt head 11 of the core rod 1 under the peritoneum.

The lead puncture needle 100 further includes an impact warning block 6, and the impact warning block 6 is mounted at a rear end of the mounting convex step 22 of the puncture needle 2. The impact warning block 6 may play a good reminding role in the surgical procedure, indicating whether a pressing action of the button is completed.

Further, the shell 51 is provided with an observation scale 59. Through the observation scale 59, medical staff may observe the advancing distance of the puncture needle 2 in real time during the puncture, and better avoid accidental injury of the surrounding tissue due to excessive puncture distance of the puncture needle 2.

The lead puncture needle 100 is made of a medical material.

The core rod 1 and the puncture needle 2 are made of a medical shape memory alloy. The core rod 1 and the puncture needle 2 made of the medical shape memory alloy may ensure that the core rod 1 and the puncture needle 2 have good elasticity during use, and better conform to the shape of the internal ring during undermining and separation.

The lead puncture needle of the present application includes the core rod 1, the puncture needle 2, the puncture safety protection mechanism 3, the lead mechanism 4 and the handle 5. The front end of the core rod 1 includes the blunt head 11 and the lead slot 12, and the lead slot 12 is arranged on the blunt head 11. The puncture needle 2 is a hollow needle, and the sharp tip 21 is arranged at the front end of the puncture needle. The core rod 1 is mounted in a hollow inner part of the puncture needle 2 and may freely move. The puncture safety protection mechanism 3 includes the safety spring 31, the safety spring rear positioning member 32 and the safety spring front positioning member 33. The safety spring 31 is mounted between the safety spring rear positioning member 32 and the safety spring front positioning member 33. The lead mechanism 4 includes the leading spring 41, the rotary positioning block 42, the stroke control member 43, the linear push block 44, and the button 45. During puncture, the safety spring 31 is compressed, and the sharp tip 21 of the puncture needle 2 is exposed to perform puncture. After the puncture is completed, under the elastic force of the safety spring 31, the blunt head 11 at the far end of the core rod 1 protrudes out of the sharp tip 21 of the puncture needle 2 for protection and avoidance of injury to the normal tissue. When the button 45 is pressed, the convex step 42-3 pushes under the stroke control convex step 43-1, and the core rod 1 moves downward, so the lead slot 12 capable of hooking the surgical suture protrudes from the sharp tip 21 of the puncture needle 2. When the button 45 is pressed again, the rotary driving block 44-1 on the linear push block 44 pushes the rotary positioning block 42 to rotate. The stroke control convex step 43-1 slides into the groove 42-2, and the core rod 1 moves upward under the elastic force of the leading spring 41. The lead slot 12 is retracted into the sharp tip 21 of the puncture needle 2 to form traction on the surgical suture. The design of the retractable smooth blunt head ensures that the blunt head may be retracted in time during puncture to expose the sharp puncture needle to facilitate puncture, and meanwhile, in the undermining and separation process, the smooth blunt head may be controlled to be exposed outside the puncture needle all the time. Therefore, accidental injury to the surrounding tissue caused by the sharp tip in the undermining and separation process is effectively avoided, and the use process is safer. Moreover, the smooth blunt head may better reduce friction in movement in the undermining process, making the undermining process smoother.

BRIEF DESCRIPTION OF THE DRAWINGS

FIG. 1-1 is an enlarged view of an area A of FIG. 1.

FIG. 2-1 is an enlarged view of an area B of FIG. 2.

FIG. 3-1 is an enlarged view of an area C of FIG. 3.

FIG. 6-1 is an enlarged view of an area D of FIG. 6.

FIG. 7-1 is an E-E cross-sectional view of FIG. 7.

FIG. 7-2 is an enlarged view of an area F of FIG. 7-1.

FIG. 7-3 is an exploded view of FIG. 7.

FIG. 8 is a schematic structure view of the lead puncture needle of FIG. 7 when the button is pressed and the lead slot is exposed to release a surgical suture.

FIG. 8-1 is a G-G cross-sectional view of FIG. 8.

FIG. 8-2 is an enlarged view of an area H of FIG. 8-1.

FIG. 9-1 is an I-I cross-sectional view of FIG. 9.

FIG. 9-2 is an enlarged view of a part J of FIG. 9-1.

FIG. 10 is a lead puncture needle of the present application including a stepping safety protection mechanism.

FIG. 11 is a lead puncture needle of the present application including a linear chute type safety protection mechanism.

FIG. 13 is a front view of FIG. 12.

FIG. 14 is a right view of FIG. 12.

FIG. 14-1 is a K-K cross-sectional view of FIG. 14.

In the above figures:

Figure 1:
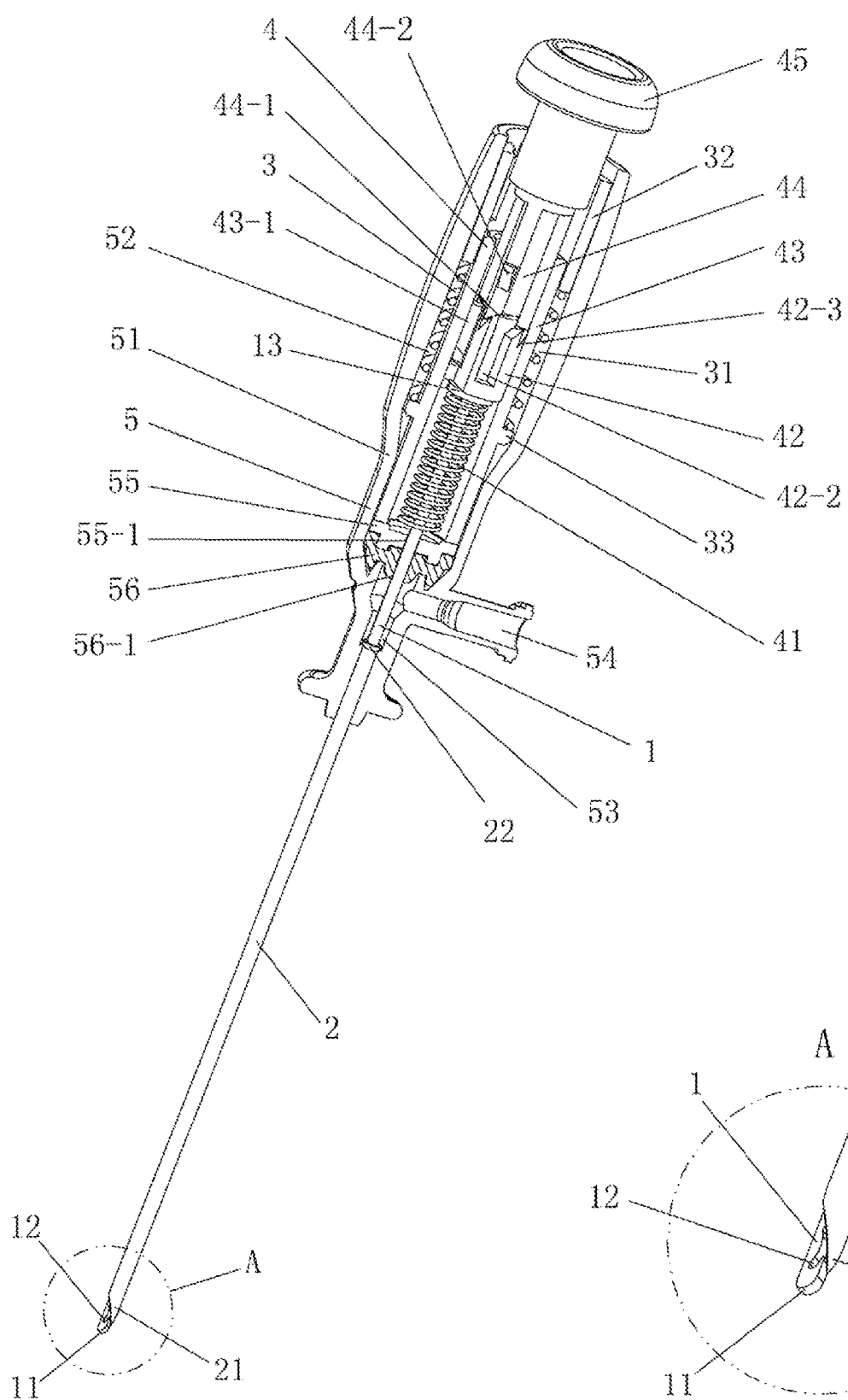
FIG. 1 is a schematic structure view of a lead puncture needle of the present application.
Figures 1, 2:
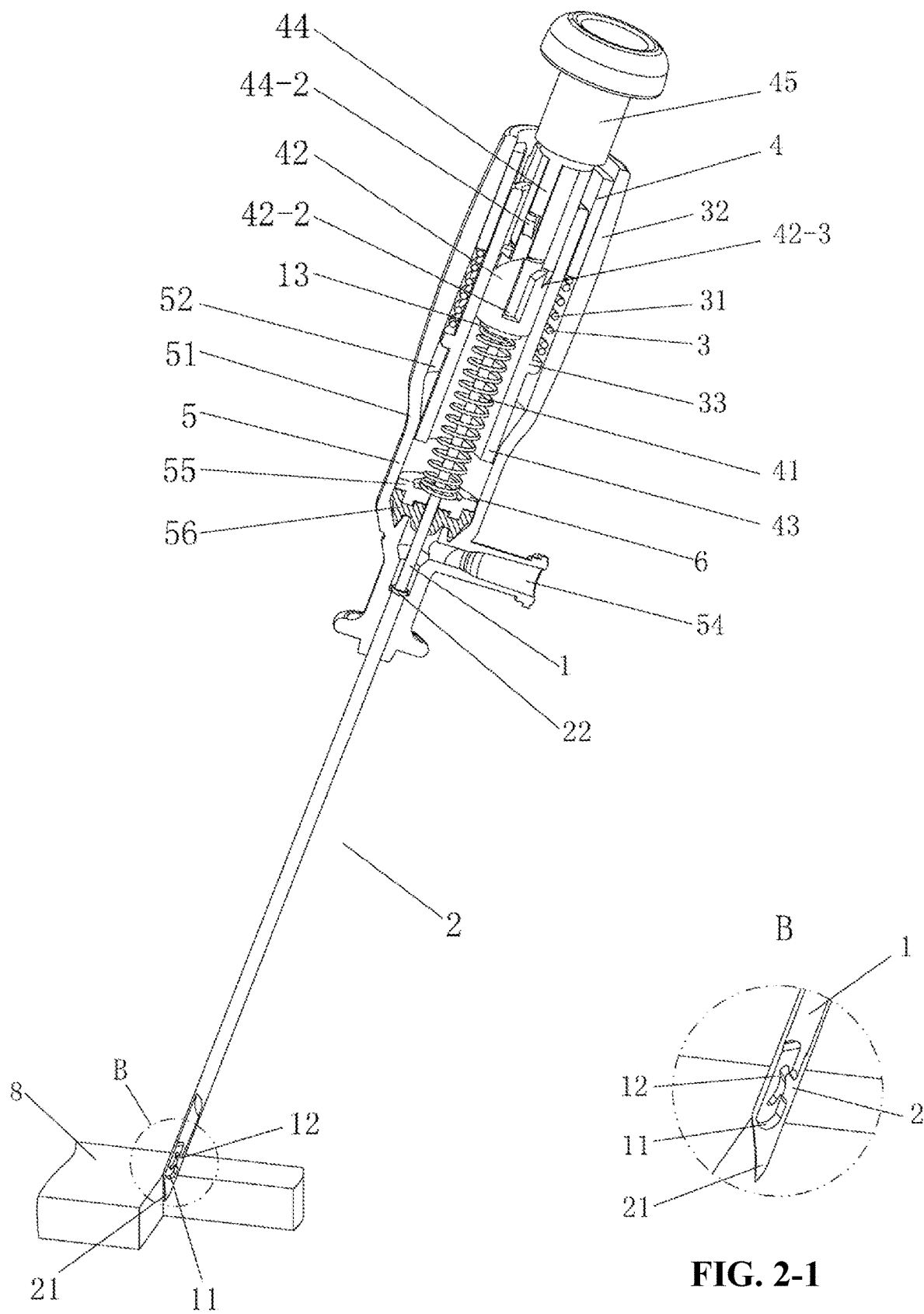
FIG. 2 is a schematic structure view of the lead puncture needle of FIG. 1 when a blunt head retracts and a sharp tip of the puncture needle is exposed.
Figures 1, 3:
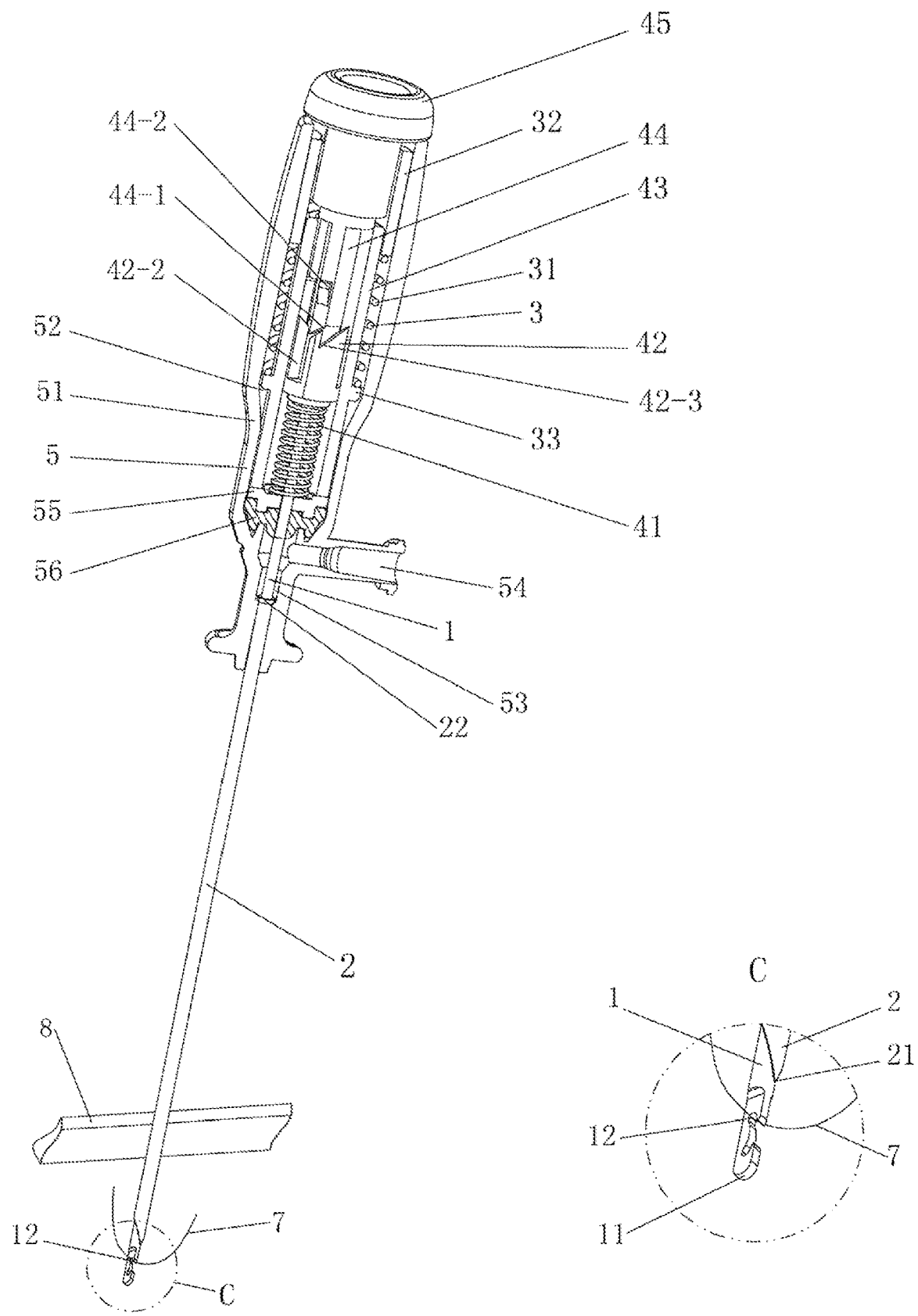
FIG. 3 is a schematic structure view of the lead puncture needle of FIG. 1 when the button is pressed and then a lead slot exposes a hanging suture.
Figure 4:
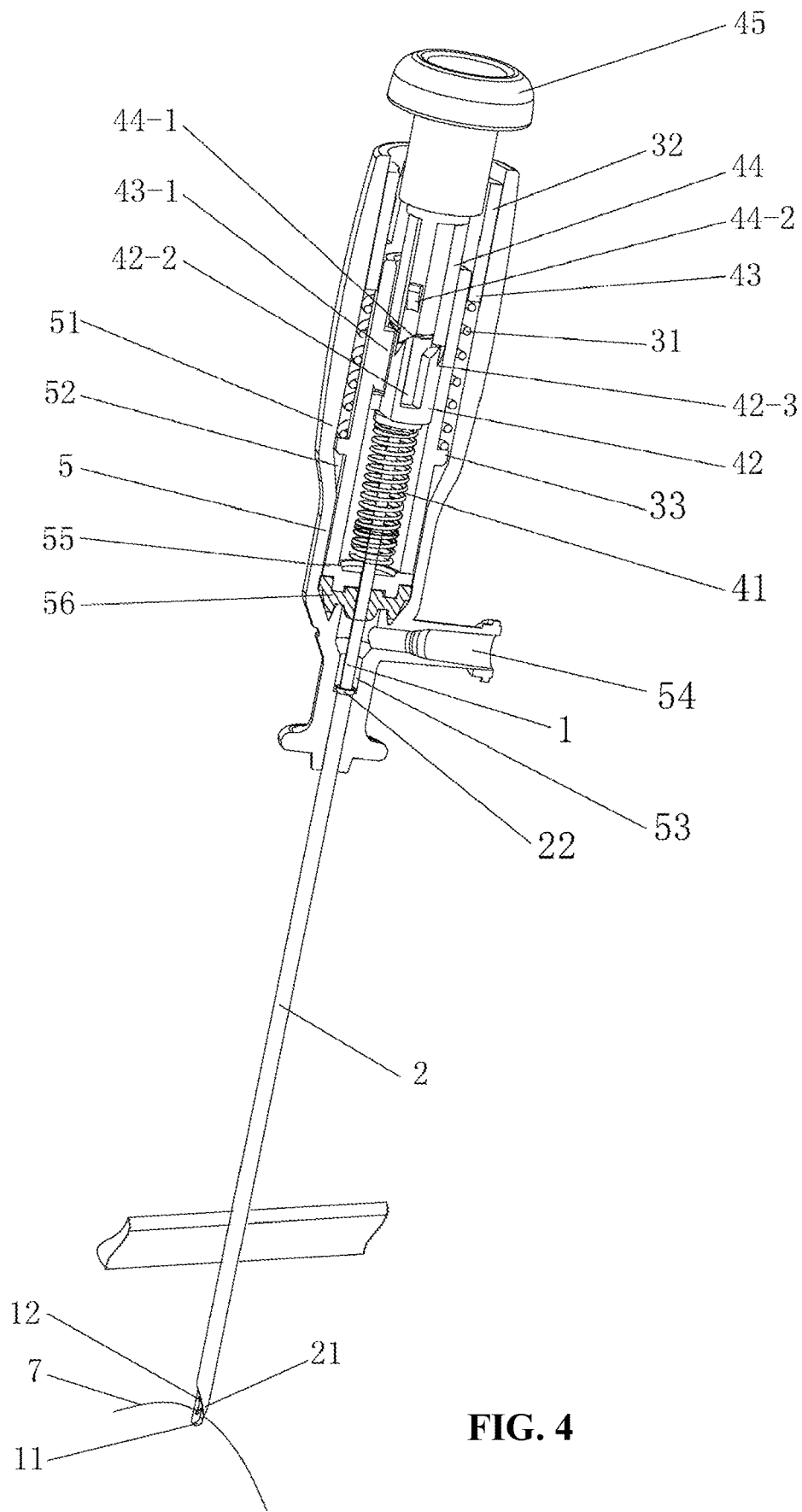
FIG. 4 is a schematic structure of the lead puncture needle of FIG. 3 when the button is pressed again and the blunt head retracts into the puncture needle.
Figure 5:
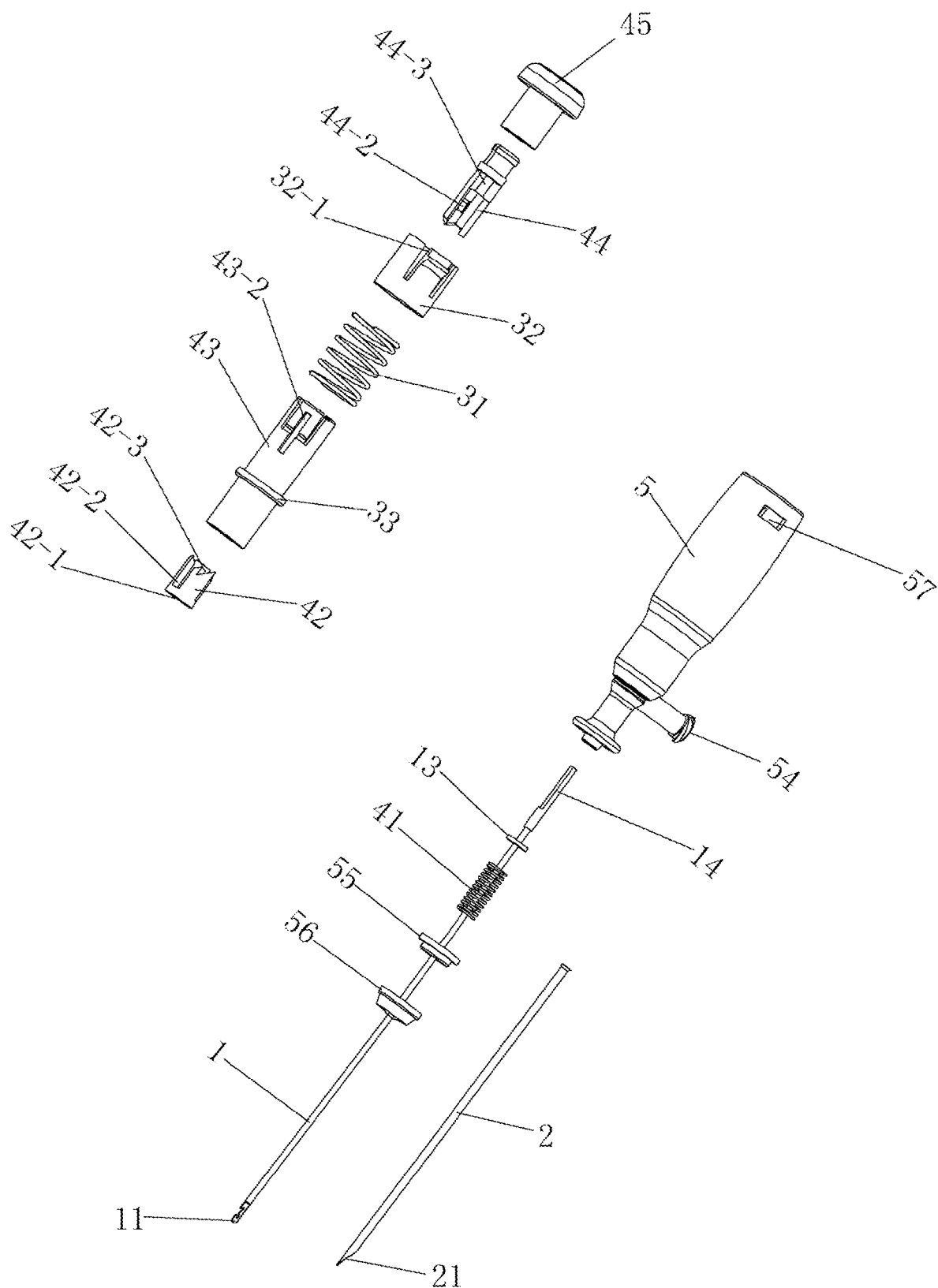
FIG. 5 is an exploded view of FIG. 1.

100 is the lead puncture needle of the present application.

1 is a core rod, 2 is a puncture needle, 3 is a puncture safety protection mechanism, 4 is a lead mechanism, 5 is a handle, 6 is a warning block, 7 is a surgical suture, and 8 is human tissue such as peritoneum 8.

11 is a blunt head, 12 is a lead slot, 13 is a positioning stopper, 14 is a rotation preventing convex step, and 15 is an infusion tank.

21 is a sharp tip, 22 is a mounting convex step, and 23 is a through hole on a pipe wall.

22-1 is a connecting end of the mounting convex step, 22-1-1 is a connecting rod, 22-2 is a limiting end of the mounting convex step, 22-2-1 is a connecting rod mounting hole, and 22-2-2 is a limiting convex step.

31 is a safety spring, 32 is a safety spring rear positioning member, 33 is a safety spring front positioning member, 34 is a shift handle, and 35 is a stroke control mechanism.

32-1 is a rear positioning member mounting convex step, 34-1 is a limiting shift button, 35-1 is a sliding block, and 35-2 is a positioning block. 35-1-1 is a convex step on the sliding block, and 35-2-2 is a limiting tooth on the positioning block.

41 is a leading spring, 42 is a rotary positioning block, 43 is a stroke control member, 44 is a linear push block, and 45 is a button.

42-1 is a central hole, 42-2 is a groove, and 42-3 is a convex step. 43-1 is a stroke control convex step, and 43-2 is a limiting groove. 44-1 is a rotary driving block, 44-2 is a limiting convex step, and 44-3 is a positioning hole.

51 is a shell, 52 is a mounting slot, 53 is a puncture needle mounting slot, 54 is an air/water inlet, 55 is a press block, 56 is a sealing member, 57 is a rear positioning member mounting hole, 58 is a shell rear cover, and 59 is an observation scale.

51-1 is a shift button movement slot, 53-1 is a limiting slot, 54-1 is an air/water channel, 54-2 is a switch, 54-3 is a fixed seat, 55-1 is a central hole of the press block, and 56-1 is a central hole of the sealing member.

DESCRIPTION OF EMBODIMENTS

Embodiment 1: Lead Puncture Needle of the Present Application

Referring to FIG. 1 to FIG. 5, in the present embodiment, the lead puncture needle 100 includes a core rod 1, a puncture needle 2, a puncture safety protection mechanism 3, a lead mechanism 4 and a handle 5.

A front end of the core rod 1 includes a blunt head 11 and a lead slot 12, and the lead slot 12 is arranged on the blunt head 11. A rear end of the core rod 1 includes a positioning stopper 13 and a rotation preventing convex step 14.

The puncture needle 2 is a hollow needle, and a sharp tip 21 is arranged at a front end of the puncture needle. The core rod 1 is mounted in a hollow inner part of the puncture needle 2 and may freely move.

The puncture safety protection mechanism 3 includes a safety spring 31, a safety spring rear positioning member 32 and a safety spring front positioning member 33. The safety spring 31 is mounted between the safety spring rear positioning member 32 and the safety spring front positioning member 33. When a resistance is present in puncture, the blunt head 11 of the core rod 1 arranged in the puncture needle 2 moves backwards under the resistance, and the safety spring 31 is compressed, causing the blunt head 11 at a far end of the core rod 1 to retract into the puncture needle 2 such that the sharp tip 21 of the puncture needle 2 is exposed to perform puncture. After tissue is punctured, the resistance disappears, and under an elastic force of the safety spring 31, the blunt head 11 at the far end of the core rod 1 protrudes out of the sharp tip 21 of the puncture needle 2 for protection and avoidance of injury to normal tissue.

The lead mechanism 4 includes a leading spring 41, a rotary positioning block 42, a stroke control member 43, a linear push block 44, and a button 45. The leading spring 41 is arranged at a front end of the rotary positioning block 42. The stroke control member 43 is a tubular structure, an inner wall of the stroke control member is provided with a stroke control convex step 43-1, and the stroke control member 43 is movably mounted in a mounting slot 52 of a shell 51 of the handle 5. The rotary positioning block 42 is provided with a central hole 42-1, a groove 42-2 and a convex step 42-3. The rear end of the core rod 1 passes through the central hole 42-1 of the rotary positioning block 42, and the rotary positioning block 42 may rotate around the core rod 1.

When the button 45 is pressed, the convex step 42-3 pushes under the stroke control convex step 43-1, and the core rod 1 moves downward, so the lead slot 12 capable of hooking a surgical suture protrudes from the sharp tip 21 of the puncture needle 2. When the button 45 is pressed again, a rotary driving block 44-1 on the linear push block 44 pushes the rotary positioning block 42 to rotate. The stroke control convex step 43-1 slides into the groove 42-2, and the core rod 1 moves upward under an elastic force of the leading spring 41. The lead slot 12 is retracted into the sharp tip 21 of the puncture needle 2 to form traction on the surgical suture.

The handle 5 includes the shell 51 and the mounting slot 52. The core rod 1, the puncture needle 2, the puncture safety protection mechanism 3, and the lead mechanism 4 are mounted in the mounting slot 52 of the shell 51.

The positioning stopper 13 of the core rod 1 is arranged at a bottom of the rotary positioning block 42, and after the rear end of the core rod 1 passes through the central hole 42-1 of the rotary positioning block 42, the rotation preventing convex step 14 of the core rod 1 is embedded in a positioning hole 44-3 on the linear push block 44.

The lead slot 12 is a bidirectional lead slot that may pull the surgical suture into tissue or pull the surgical suture out of the tissue. When the core rod 1 moves forward, the surgical suture 7 is placed at a rear end of the lead slot 12. When the core rod 1 moves backward, the surgical suture 7 is placed at a front end of the lead slot 12. The lead slot 12 may realize leading when the core rod 1 advances or retreats in two directions.

The puncture needle 2 includes a mounting convex step 22, and a puncture needle mounting slot 53 is arranged on the shell 51. The puncture needle 2 is mounted in the puncture needle mounting slot 53 on the shell 51 by bonding through the mounting convex step 22.

The spring front positioning member 33 is integrally fabricated with the stroke control member 43 into a whole, and fabrication and assembly processes are more convenient. Of course, the spring front positioning member 33 may also be detachably connected to the stroke control member 43. The spring front positioning member 33 may be connected to the stroke control member 43 by screw connection, concave-convex clamp fit connection, interference fit connection, bonding, or the like. Other connection modes may be adopted by those skilled in the art without departing from the scope of protection of the present application.

The spring rear positioning member 32 is provided with a positioning member mounting convex step 32-1. The positioning member mounting convex step 32-1 is embedded in a positioning member mounting hole on the handle 5 to realize mounting and connection of the spring rear positioning member 32 and the handle.

A limiting convex step 44-2 is arranged on the linear push block 44. The limiting convex step 44-2 cooperates with a limiting groove 43-2 on the stroke control member 43 to effectively prevent the linear push block 44 from being accidentally detached from the stroke control member 43 during use.

In the present embodiment, the linear push block 44 and the button 45 are connected together by concave-convex clamp fit. Of course, the linear push block 44 and the button 45 may be fabricated into a whole, or connected together by other means such as screw connection, interference fit, bonding, and the like, without departing from the scope of protection of the present application.

In the present embodiment, the shell 51 is also provided with an air/water inlet 54, a press block 55 and a sealing member 56.

Further, one end of the leading spring 41 is connected to the positioning stopper 13 at the rear end of the core rod 1, and the other end is connected to the press block 55 of the shell 51.

The core rod 1 passes through a central hole 55-1 of the press block 55 and a central hole 56-1 of the sealing member 56. The press block 55 presses the sealing member 56. The sealing member 56 forms dynamic seal for the core rod 1. When surgery under a laparoscope is performed, firstly it is necessary to inject air into the abdominal cavity through the air/water inlet 54 to form pneumoperitoneum, and at the same time, it is necessary to ensure the stability of the pneumoperitoneum during the surgery. The dynamic seal design may ensure the stability of the pneumoperitoneum well during the surgery and ensure smooth progress of the surgery.

During the surgery, after the puncture needle 2 punctures an abdominal wall, the blunt head 11 at the far end of the core rod 1 protrudes out of the sharp tip 21 of the puncture needle 2, and then a doctor operates the blunt head 11 to undermine and separate the peritoneum under the abdominal wall. Since a gap between the abdominal wall and the peritoneum is very small, in order to facilitate the advancement of the core rod 1, a small amount of normal saline may be injected into a surgical site via a head part of the puncture needle 2 through the air/water inlet 54. Under the action of the normal saline, local separation appears between the abdominal wall and the peritoneum, thereby facilitating undermining and separation of the blunt head 11 of the core rod 1 outside the peritoneum.

If it is not necessary to form pneumoperitoneum during the surgery, the press block 55 and the sealing member 56 may not need to be mounted.

In the present embodiment, the impact warning block 6 is an end surface of the press block 55. During the movement, the bottom of the stroke control member 43 and the end surface of the press block 55 collide, and a warning sound is given, which may play a good warning and reminding role during the surgery.

In the present embodiment, the core rod 1 and the puncture needle 2 are made of a medical shape memory alloy, ensuring that the core rod 1 and the puncture needle 2 have good elasticity during use, and the core rod 1 and the puncture needle 2 better conform to the shape of the internal ring during undermining and separation.

When in use, the surgical suture 7 is threaded into the lead slot of the core rod 1, and then the skin is punctured. At this time, the blunt head 11 of the core rod 1 moves backwards under skin resistance, and the positioning stopper 13 of the core rod 1 pushes the rotary positioning block 42 to drive the stroke control member 43, the linear push block 44 and the handle 45 to move backward together. At this time, the spring front positioning member 33 arranged on the stroke control member 43 moves backward to compress the safety spring 31, causing the blunt head 11 at the far end of the core rod 1 to retract into the puncture needle 2 such that the sharp tip 21 of the puncture needle 2 is exposed to perform puncture, referring to FIG. 2. When the puncture is completed, the resistance disappears. At this time, under the resilience of the safety spring 31, the spring front positioning member 33 moves forward to drive the stroke control member 43 to restore forward, and drive the linear push block 44 and the handle 45 to restore forward together. The core rod 1 restores to the initial state under the restoring force, and the blunt head 11 at the far end of the core rod 1 protrudes out of the sharp tip 21 of the puncture needle 2 for protection again and avoidance of injury to normal tissue.

At this time, the button 45 is pressed to drive the linear push block 44 to move downward. The rotary driving mechanism 44-1 of the linear push block 44 pushes the rotary positioning block 42 to rotate, and the convex step 42-3 pushes under the stroke control convex step 43-1. The core rod 1 moves downward so that the lead slot 12 capable of hooking the surgical suture protrudes from the sharp tip 21 of the puncture needle 2. The button 45 is pressed and held, the lead puncture needle of the present application extraperitoneally undermines along the inner semi-circumference of the internal ring and separates to the rear side of the internal ring to puncture into the peritoneum 8, and then the surgical suture 7 is released. It is necessary to ensure that the blunt head 11 of the core rod 1 is exposed to the outer part of the sharp tip 21 of the puncture needle 2 in the undermining and separating process all the time until reaching the peritoneum 8, referring to FIG. 3. Under a resistance of the peritoneum 8, the core rod 1 retracts, and the peritoneum 8 is punctured by the sharp tip 21 of the puncture needle 2. Since the end of the core rod 1 adopts a smooth blunt-head design, accidental injury to the surrounding tissue in the undermining and separating process may be well avoided. In particular, accidental injury to important parts such as arteries may be avoided. When reaching the peritoneum 8, since a large puncture force is required for puncturing the peritoneum 8, at this time, the core rod 1 retracts into the puncture needle 2 under a large resistance, and the sharp tip 21 of the puncture needle 2 is used to perform puncture.

After release, the lead puncture needle 100 is retracted to the needle insertion part of the internal ring, and then the button 45 is pressed and held. The lead puncture needle 100 extraperitoneally undermines along the outer semi-circumference of the internal ring and separates to the rear side of the internal ring to puncture into the peritoneum 8. The surgical suture 7 is placed into the lead slot 12 at the front end of the core rod 1 again. The button 45 is pressed, and the rotary driving block 44-1 on the linear push block 44 pushes the rotary positioning block 42 to rotate. The stroke control convex step 43-1 slides into the groove 42-2, and the core rod 1 moves upward under the elastic force of the leading spring 41. The lead slot 12 is retracted into the sharp tip 21 of the puncture needle 2, and the lead puncture needle 100 is retracted backward. The core rod 1 drives the surgical suture 7 to be led out of the body, knotted and fixed, referring to FIG. 4.

The entire surgical procedure is completed by only the lead puncture needle of the present application. The lead puncture needle of the present application has the advantages of being simple and convenient compared with the condition that multiple instruments are needed in the current surgical procedure to complete the surgical procedure. In particular, the design of the retractable smooth blunt head ensures that the blunt head may be retracted in time during puncture to expose the sharp puncture needle to facilitate puncture, and furthermore, in the undermining and separation process, the smooth blunt head may be controlled to be exposed outside the puncture needle all the time. Therefore, accidental injury to the surrounding tissue caused by the sharp tip in the undermining and separation process is effectively avoided, and the use process is safer. Moreover, the smooth blunt head may better reduce friction in movement in the undermining process, making the undermining process smoother.

Figure 6:
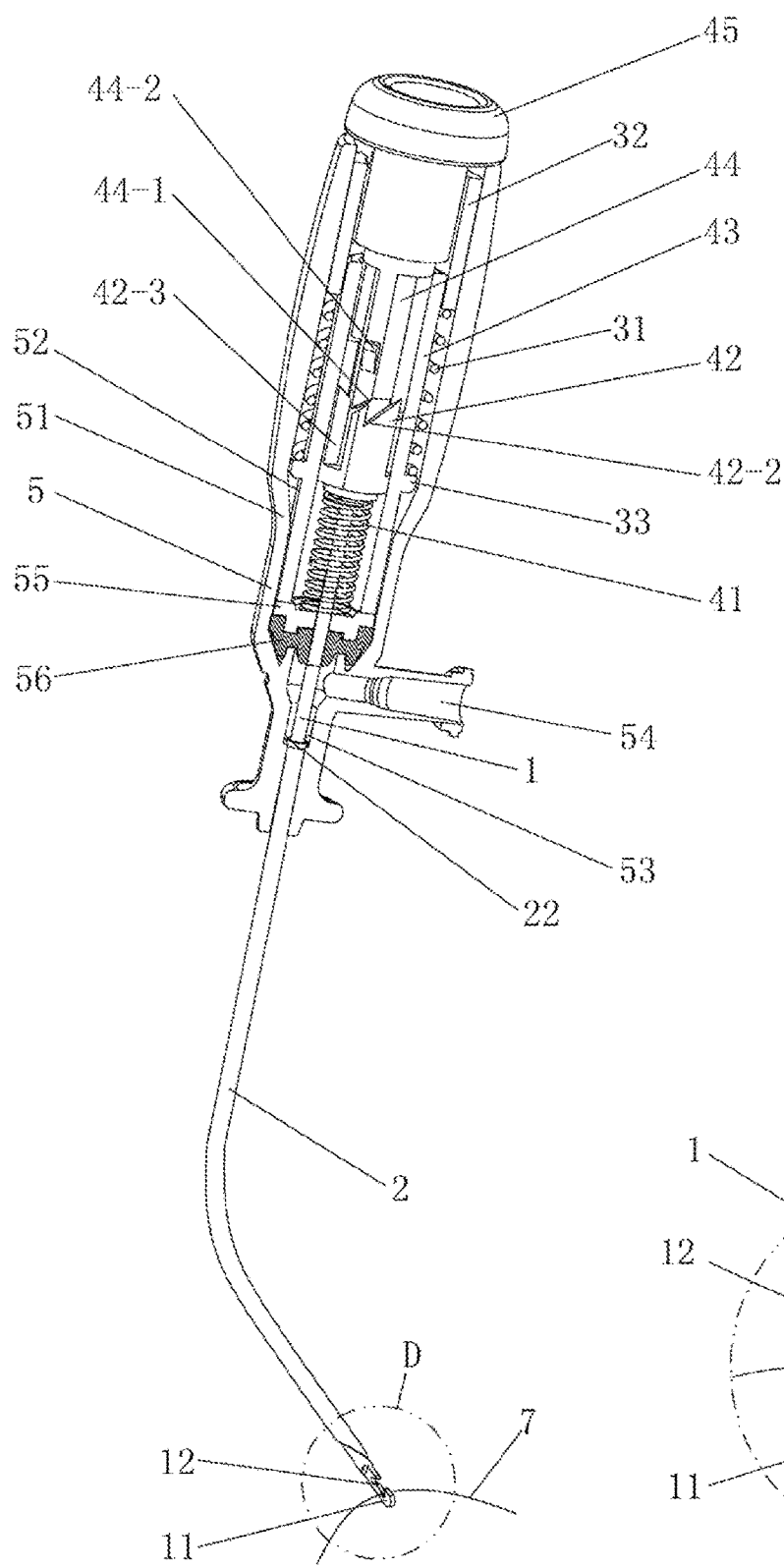
FIG. 6 is a schematic structure view of an arc-shaped lead puncture needle of the present application.
Figures 3, 7:
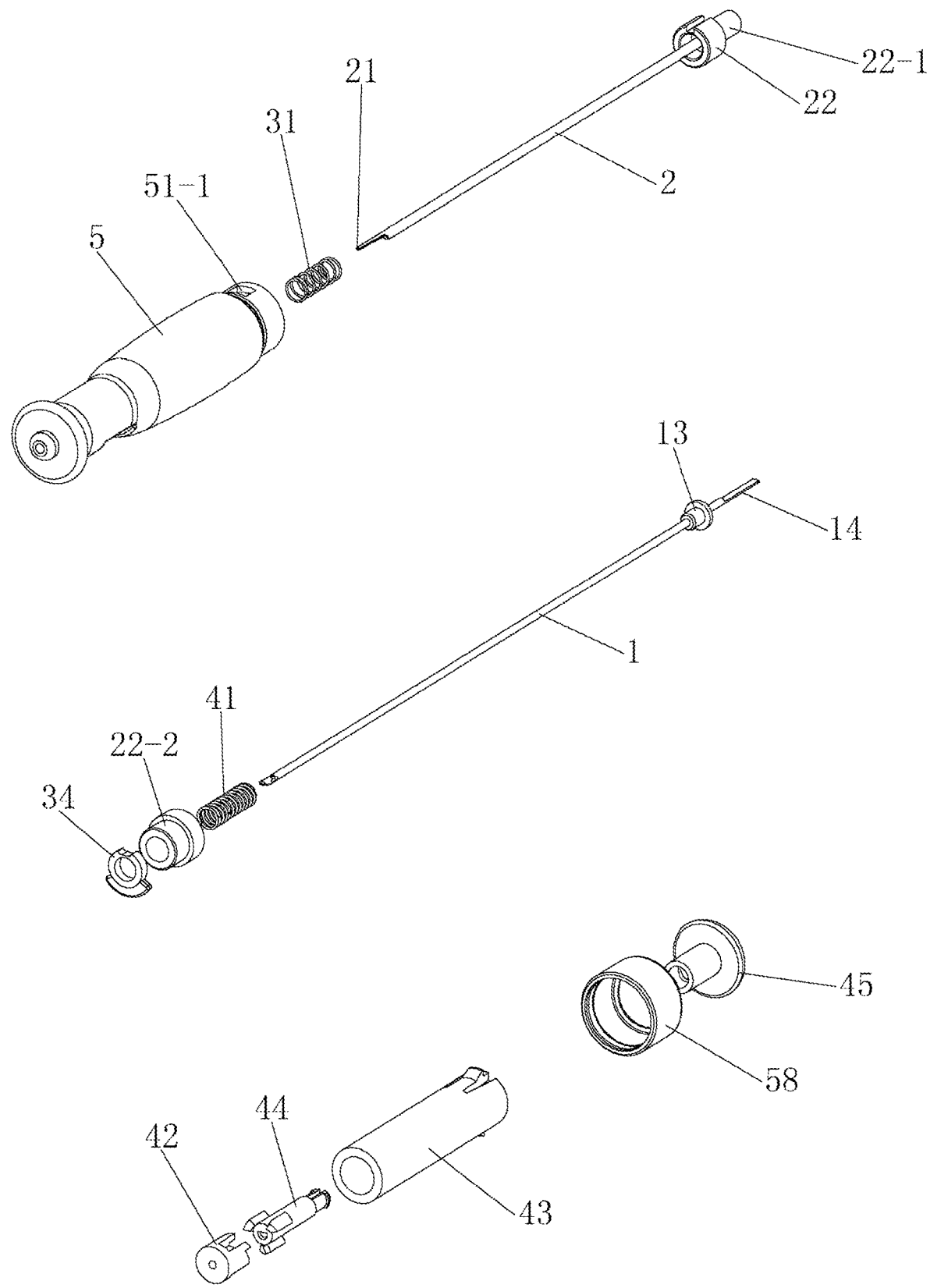
FIG. 7 is a schematic structure view of a lead puncture needle of the present application with a front type safety mechanism.
Figures 1, 2, 9:
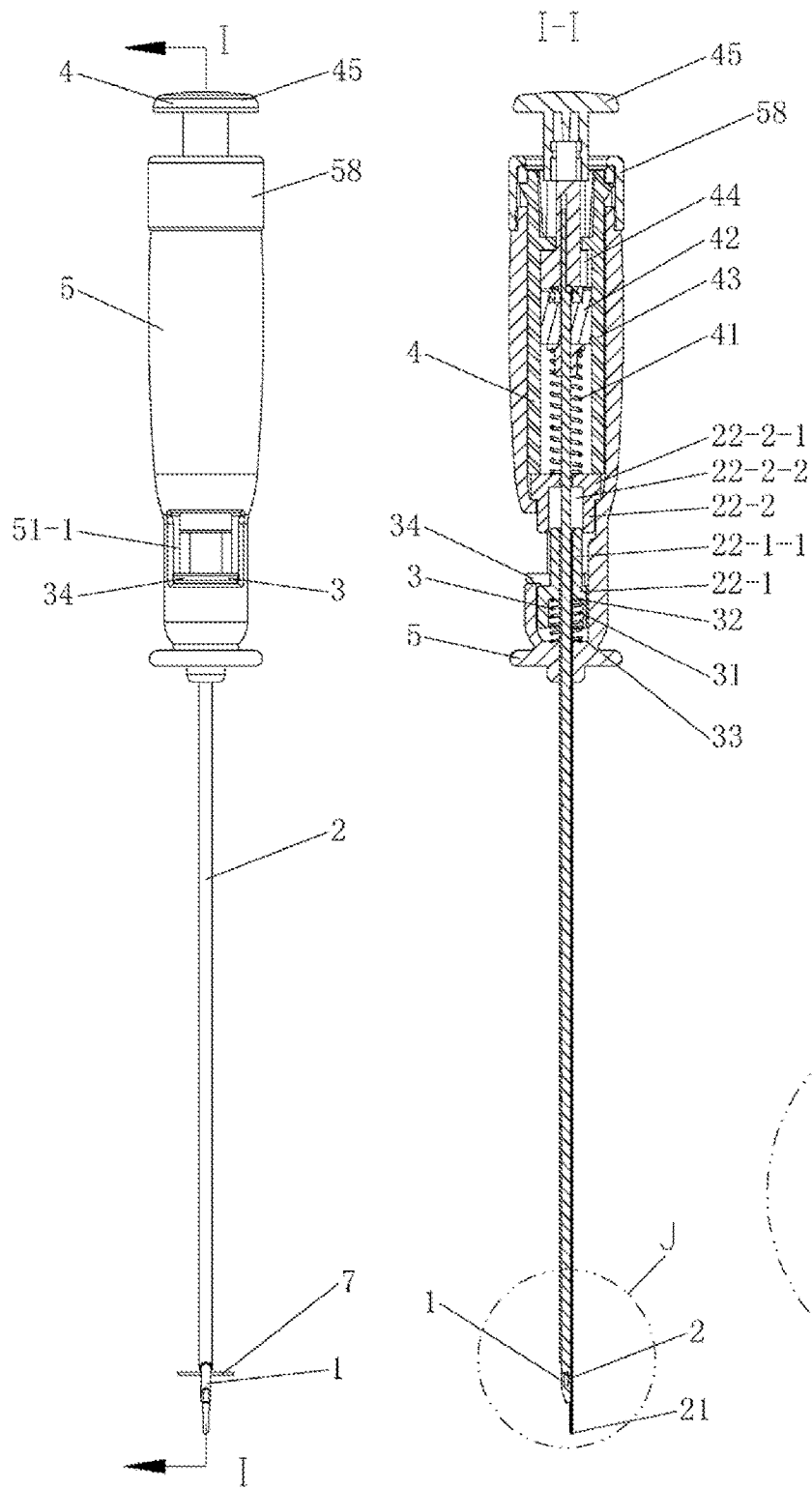
FIG. 9 is a schematic structure view of the lead puncture needle of FIG. 7 when a shift handle is pushed forward for puncture.
Figure 12:
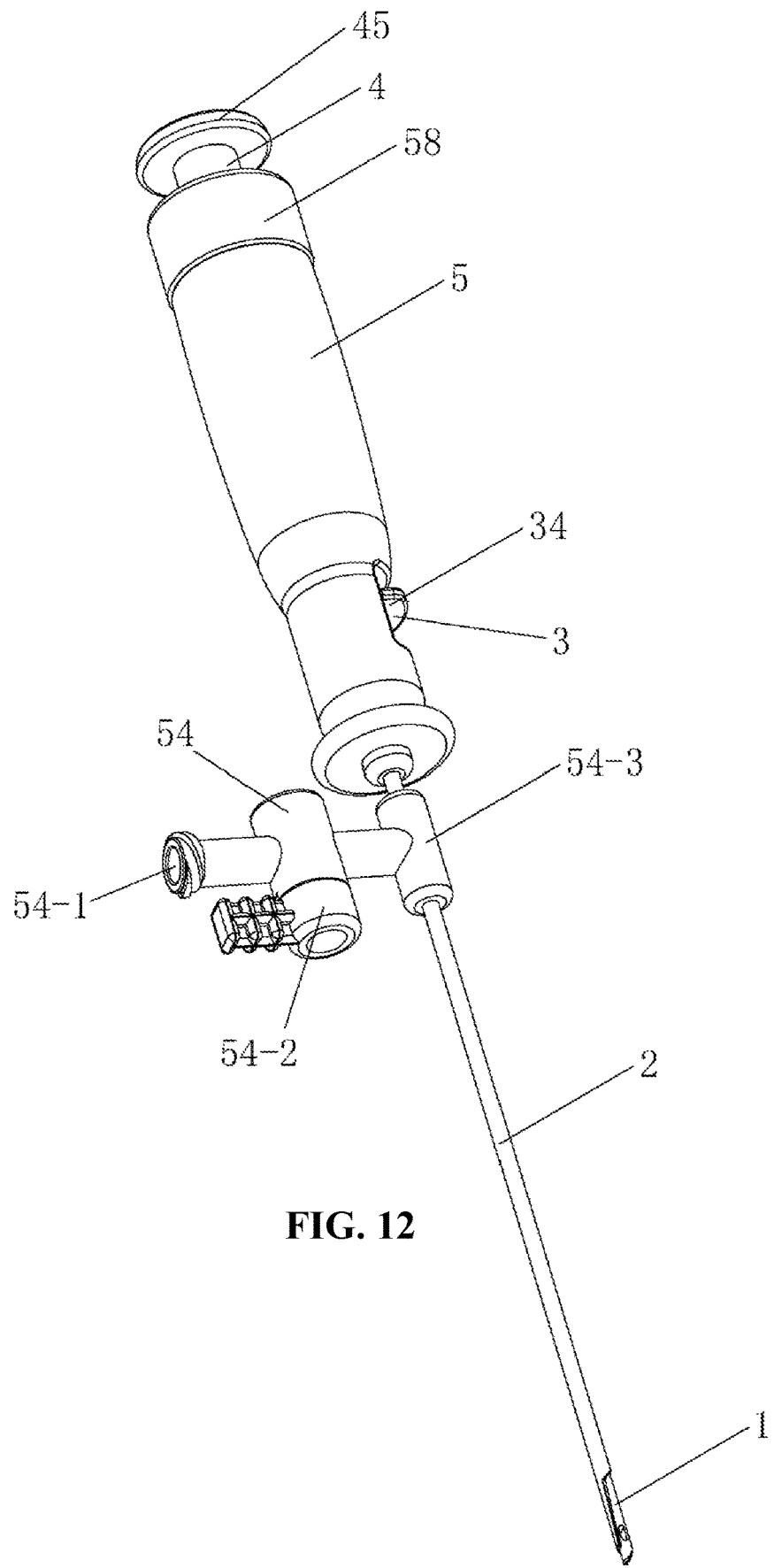
FIG. 12 is a schematic structure view of a lead puncture needle of the present application with a front type safety mechanism and an air/water inlet.
Figure 15:
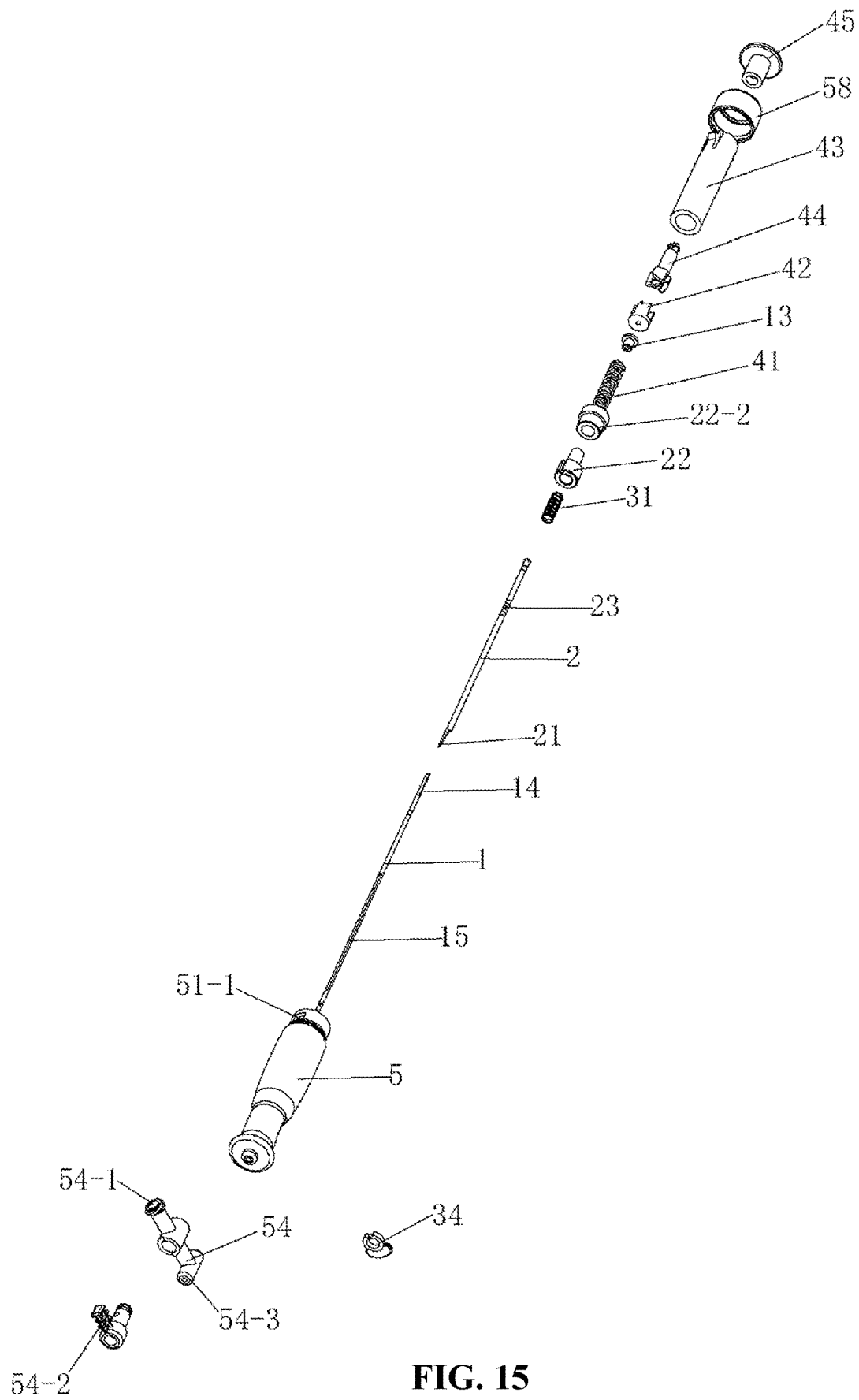
FIG. 15 is an exploded view of FIG. 12.

In the present embodiment, the core rod 1 and the puncture needle 2 adopt a linear design. Because in the surgical procedure, the surgical suture needs to undermine along the outer semi-circumference of the internal ring and separate to the back side of the internal ring, the core rod 1 or the puncture needle 2 may be designed into special geometric shapes in accordance with clinical requirements, such as a linear shape, an arc shape, an L shape, a C shape, a U shape, an S shape and the like, to facilitate the surgical procedure. FIGS. 6 and 6-1 show the core rod 1 and the puncture needle 2 with an arc-shaped structure.

Embodiment 2: Leading Puncture Needle of the Present Application with Front Type Safety Protection Mechanism Referring to FIG. 7 to FIG. 9-2, the difference between the present embodiment and Embodiment 1 is that, in the present embodiment, the puncture safety protection mechanism 3 is front-mounted. The safety spring 31, the safety spring rear positioning member 32 and the safety spring front positioning member 33 forming the puncture safety protection mechanism 3 are mounted in the puncture needle mounting slot 53 at the front end of the stroke control member 43. The puncture safety protection mechanism 3 further includes a shift handle 34. When the shift handle 34 is pushed forward, the safety spring 31 is compressed, the puncture needle 2 moves forward, and the sharp tip 21 of the puncture needle 2 is exposed to perform puncture. After the puncture is completed, the shift handle 34 is released. Under the elastic force of the safety spring 31, the puncture needle 2 moves backward, the blunt head 11 at the far end of the core rod 1 is placed out of the sharp tip 21 of the puncture needle 2 for protection and avoidance of accidental injury to normal tissue.

The shift handle 34 includes a limiting shift button 34-1, the shell 51 of the handle 5 is provided with a shift button movement slot 51-1, and the limiting shift button 34-1 may move back and forth in the shift button movement slot 51-1.

The shift handle 34 may be integrally fabricated on the puncture needle 2 or may be detachably connected to the puncture needle 2.

In the present embodiment, the shift handle 34 is connected to the puncture needle 2 by concave-convex clamp fit connection. The shift handle 34 may also be connected to the puncture needle 2 by screw connection, interference fit connection, bonding, or the like. Or, other connection modes may be devised by those skilled in the art according to actual needs without departing from the claimed protection scope of the application.

In the present embodiment, the mounting convex step 22 includes a connecting end 22-1 and a limiting end 22-2, the connecting end 22-1 includes a connecting rod 22-1-1, and the limiting end 22-2 includes a connecting rod mounting hole 22-2-1 and a limiting convex step 22-2-2. The puncture needle mounting slot 53 is provided with a limiting slot 53-1. The connecting rod 22-1-1 may be mounted in the connecting rod mounting hole 22-2-1, and the limiting convex step 22-2-2 of the limiting end 22-2 may be mounted in the limiting slot 53-1, that is, the puncture needle 2 is mounted in the puncture needle mounting slot 53.

The safety spring front positioning member 33 is arranged at the far end of the puncture needle mounting slot 53 of the handle 5. The safety spring rear positioning member 32 is arranged at the near end of the puncture needle mounting slot 53. In the present embodiment, the bottom of the puncture needle mounting slot 53 is directly arranged as the safety spring front positioning member 33, and the bottom of the connecting end 22-1 of the puncture needle 2 is arranged as the safety spring rear positioning member 32. The safety spring 31 is mounted between the mounting convex step 22 of the puncture needle 2 and the bottom of the puncture needle mounting slot 53 of the handle.

Of course, the safety spring front positioning member 33 may be separately designed and mounted at the far end of the puncture needle mounting slot 53, or the safety spring rear positioning member 32 is separately designed and mounted at the near end of the connecting end 22-1 of the puncture needle 2, which will not be described by way of example.

In the present embodiment, the handle 5 is provided with a back cover 58. After the core rod 1, the puncture needle 2, the puncture safety protection mechanism 3, and the lead mechanism 4 are mounted in the mounting slot 52, the lead puncture needle 100 is assembled into a whole by covering the back cover 58.

When in use, the surgical suture 7 is threaded into the lead slot 12 of the core rod 1. The shift handle 34 is pushed forward, the safety spring 31 is compressed, the puncture needle 2 moves forward, and the sharp tip 21 is exposed to perform puncture, referring to FIG. 9, FIG. 9-1 and FIG. 9-2. After the puncture is completed, the shift handle 34 is released. Under the elastic force of the safety spring 31, the puncture needle 2 moves backward, the blunt head 11 at the far end of the core rod 1 protrudes out of the sharp tip 21 of the puncture needle 2 for protection and avoidance of injury to normal tissue, referring to FIG. 7. The blunt head 11 is kept in a protruded state, the lead puncture needle of the present application extraperitoneally undermines along the inner circumference of the inner ring and separates to the peritoneum 8 at the rear side of the inner ring, and then the shift handle 34 is pushed forward. The safety spring 31 is compressed, the puncture needle 2 moves forward, and the sharp tip 21 is exposed to puncture the peritoneum 8, referring to FIG. 9 to FIG. 9-2. After the puncture is completed, the shift handle 34 is released. Under the elastic force of the safety spring 31, the sharp tip 21 of the puncture needle 2 is retracted, and the blunt head 11 is exposed to prevent accidental injury.

At this time, the button 45 is pressed to drive the linear push block 44 to move downward. The rotary driving mechanism 44-1 of the linear push block 44 pushes the rotary positioning block 42 to rotate, and the convex step 42-3 pushes under the stroke control convex step 43-1. The core rod 1 moves downward so that the lead slot 12 protrudes from the sharp tip 21 of the puncture needle 2. The surgical suture 7 in the lead slot 12 is released, referring to FIG. 8, FIG. 8-1 and FIG. 8-2. Then, the button 45 is pressed again, and the rotary driving block 44-1 on the linear push block 44 pushes the rotary positioning block 42 to rotate. The stroke control convex step 43-1 slides into the groove 42-2, and the core rod 1 moves upward under the elastic force of the leading spring 41. The lead slot 12 is retracted into the sharp tip 21 of the puncture needle 2, and the lead puncture needle 100 is retracted backward to the needle insertion part of the inner ring.

Then, the lead puncture needle 100 extraperitoneally undermines along the outer circumference of the inner ring and separates to the peritoneum 8 at the rear side of the inner ring. The shift handle 34 is pushed forward, the safety spring 31 is compressed, the puncture needle 2 moved forward, and the sharp tip 21 is exposed to puncture the peritoneum 8. After the puncture is completed, the shift handle 34 is released, and the sharp tip 21 of the puncture needle 2 is retracted. Then, the button 45 is pressed so that the lead slot 12 protrudes from the sharp tip 21 of the puncture needle 2. The surgical suture 7 is placed into the lead slot 12 at the front end of the core rod 1 again. Then, the button 45 is pressed, the lead slot 12 is retracted into the puncture needle 2, and referring to FIG. 7, FIG. 7-1 and FIG. 7-2, the lead puncture needle 100 is retracted backward. The core rod 1 drives the surgical suture 7, and the surgical suture 7 is led out of the body, knotted and fixed.

Compared with Embodiment 1, in the present embodiment, when the lead puncture needle 100 is in a free state, the sharp tip 21 of the puncture needle 2 is in a retracted state, and the blunt head 11 of the core rod 1 may play a good protection role. Only when a medical worker consciously pushes the shift handle 34 forward, the sharp tip 21 of the puncture needle 2 may be exposed to perform puncture. Therefore, in the undermining and separating process, the medical worker does not need to press and hold the button 45 all the time as in Embodiment 1 to keep the blunt head 11 of the core rod 1 exposed all the time. The medical worker may be better prevented from accidentally exposing the sharp tip 21 of the puncture needle 2 due to accidental relaxation of the button 45 in the undermining and separation process. Especially, when tough tissue such as the peritoneum is punctured, the sharp tip 21 of the puncture needle 2 may be effectively prevented from rushing due to excessive force in the puncturing process, thereby avoiding accidental injury of the surrounding tissue. The use process is safer and the lead puncture needle is more convenient for the medical worker to use.

Embodiment 3: Leading Puncture Needle of the Present Application with Manual Safety Protection Mechanism Referring to FIG. 10 and FIG. 11, the difference between the present embodiment and Embodiment 2 is that, in the present embodiment, the puncture safety protection mechanism 3 is a manual safety protection mechanism.

Referring to FIG. 10, in the present embodiment, the stroke control mechanism 35 is a linear stepping mechanism. The safety protection mechanism 3 includes a shift handle 34 and a stroke control mechanism 35. The stroke control mechanism 35 includes a sliding block 35-1 and a limiting block 35-2. Intermittent sliding is formed between the sliding block 35-1 and the limiting block 35-2.

A total stroke of the stroke control mechanism 35 is generally controlled to be 1 mm-15 mm, and the spacing of each step is generally 1 mm-5 mm. The total stroke control of the stroke control mechanism 35 may prevent the puncture needle 2 from accidentally injuring the surrounding tissue due to excessive puncture depth in the puncture process.

A concave-convex fit type intermittent sliding mechanism is arranged between the sliding block 35-1 and the limiting block 35-2.

The sliding block 35-1 of the stroke control mechanism 35 is provided with a convex step 35-1-1.

The limiting block 35-2 is provided with a limiting tooth 35-2-1 matched with the convex step 35-1-1. The limiting tooth 35-2-1 may be embedded in a gap of the convex step 35-1-1 to play a positioning role. The spacing between two adjacent convex steps 35-1-1 is a movement step length of the sliding block 35-1. The movement step length of the sliding block 35-1 is controlled to be 1 mm-5 mm, so that every time when the shift handle 34 is pushed forward, the step length of the forward movement of the puncture needle 2 is also controlled to be 1 mm-5 mm.

When the shift handle 34 is pushed forward, the sliding block 35-1 is driven to move forward. The presence of the limiting block 35-2 causes the sliding block 35-1 to move a bar of distance each time to form intermittent stepping movement. The distance of each advancement is the spacing between adjacent convex steps 35-1-1 of the sliding block 35-1. Due to the limitation of the stepping spacing, the protrusive length of the sharp tip 21 of the puncture needle 2 every time may be better controlled, and the safety during the observation may be improved. Conversely, when the shift handle 34 is pulled backward, intermittent backward sliding movement is formed.

The small step length of the sliding block 35-1 is designed so that every time when the shift handle 34 is pushed forward in the puncture process, the distance that the puncture needle 2 advances is controlled within the step length range. Therefore, accidental injury to surrounding tissue due to excessively fast puncture speed in the puncture process is effectively prevented, and the use process is safer.

Referring to FIG. 10, in case of use, when puncture needs to be performed, the shift handle 34 is pushed forward. The sliding block 35-1 of the stroke control mechanism 35 advances according to a designed step length range to drive the puncture needle 2 to move forward, and the sharp tip 21 of the puncture needle 2 is exposed to perform puncture. When it is necessary to undermine along the outer side of the peritoneum and separate the tissue, the shift handle 34 is retracted. The puncture needle 2 is retracted backward under driving of the stroke control mechanism 35, and the sharp tip 21 of the puncture needle 2 is retracted to expose the blunt head of the core rod 1 to realize protection in the undermining and separation process.

Referring to FIG. 11, the stroke control mechanism 35 may also be a linear chute mechanism. The front and rear ends of the shift button movement slot 51-1 form a limiting block 35-1 of the stroke control mechanism 35, and the shift handle 34 may drive the sliding block 35-1 to slide back and forth in the shift button movement slot 51-1. The shell 51 is provided with an observation scale 59. The distance of advancement or retraction of the puncture needle 2 is controlled by a value on the observation scale 59.

In addition, the stroke control mechanism 35 may also be a spiral progressive mechanism. The distance over which the puncture needle 2 advances is adjusted by rotating the shift handle 34. Of course, other various structures designed by those skilled in the art according to actual conditions do not depart from the scope of protection of the present patent application.

Embodiment 4: Leading Puncture Needle of the Present Application Including Front Type Safety Protection Mechanism and Water Inlet Referring to FIG. 12 to FIG. 15, the difference between the present embodiment and Embodiment 2 is that, in the present embodiment, the lead puncture needle 100 is provided with a gas/water inlet 54. Air or liquid may be injected into the abdominal cavity through the gas/water inlet 54.

In the present embodiment, the gas/water inlet 54 includes a gas/water channel 54-1, a switch 54-2 and a fixed seat 54-3.

A through hole 23 is formed in a pipe wall of the puncture needle 2. An infusion tank 15 is axially formed at an outer surface of the core rod 1 corresponding to the water inlet 23.

During mounting, an outlet of the gas/water channel 54-1 of the gas/water inlet 54 is aligned with the water inlet 23, and is fixed to the puncture needle by the fixed seat 54-3, referring to FIG. 14-1.

When gas needs to be injected into the abdominal cavity to form pneumoperitoneum, the gas/water inlet 54 is connected to a gas source, and the switch 54-2 is turned on. Through the through hole 23 in the puncture needle 2, the gas is injected into the abdominal cavity to form pneumoperitoneum.

When liquid, such as normal saline, needs to be injected into the abdominal cavity, the gas/water inlet 54 is connected to a normal saline bag, and the switch 54-2 is turned on. The normal saline enters the puncture needle 2 through the through hole 23 via the gas/water channel 54-1, and then reaches a surgical site at the head of the core rod 1 along the infusion tank 15 formed axially. Under the action of the normal saline, local separation appears between the abdominal wall and the peritoneum, thereby facilitating the blunt head 11 of the core rod 1 to extraperitoneally undermine and separate.

In the present embodiment, since the gas/water inlet 54 is also arranged, different requirements for injecting gas or liquid into the abdominal cavity during the surgery may be satisfied, and the surgical operation process is more convenient.

It should be noted that the structures disclosed and described herein may be replaced with other structures having the same effect, and the embodiments described herein are not the only structures that can implement the present application. Although the preferred embodiments of the present application have been introduced and described herein, it will be apparent to those skilled in the art that these embodiments are merely illustrative, and numerous variations, modifications, and replacements may be made by those skilled in the art without departing from the present application. Therefore, the protection scope of the present application should be subject to the spirit and scope of the appended claims of the present application.

The invention claimed is:

1. A lead puncture needle comprising:
a core rod;
a puncture needle;
a puncture safety protection mechanism;
a lead mechanism; and
a handle, wherein:
  A. a front end of the core rod comprises a blunt head and a lead slot, and the lead slot is arranged on the blunt head;
  B. the puncture needle is a hollow needle, and a sharp tip is arranged at a front end of the puncture needle; and the core rod is mounted in the puncture needle, and the puncture needle and the core rod are configured to move relative to each other;
  C. the lead mechanism comprises a leading spring, a rotary positioning block, a stroke control member, a linear push block, and a button; the stroke control member is a tubular structure, a tube wall thereof is provided with a stroke control convex step, and the stroke control member is movably mounted in a mounting slot of a shell of the handle; the leading spring is arranged at a front end of the rotary positioning block; the rotary positioning block is provided with a central hole, a groove and a convex step; a rear end of the core rod passes through the central hole of the rotary positioning block, and the rotary positioning block is configured to rotate around the core rod; when the button is pressed, the convex step pushes under the stroke control convex step, the core rod moves downward, and the leading spring is compressed, so that the lead slot capable of hooking a surgical suture protrudes from the sharp tip of the puncture needle; when the button is pressed again, a rotary driving block on the linear push block pushes the rotary positioning block to rotate, the stroke control convex step slides into the groove, the core rod moves upward under an elastic force of the leading spring, and the lead slot is retracted into the sharp tip of the puncture needle to prevent the surgical suture from slipping off and form traction on the surgical suture; and D. the handle comprises the shell and the mounting slot; and the core rod, the puncture needle, the puncture safety protection mechanism, and the lead mechanism are mounted in the mounting slot of the shell.

2. The lead puncture needle according to claim 1, wherein the rear end of the core rod is provided with a positioning stopper and a rotation preventing convex step for preventing the rotation of the core rod.

3. The lead puncture needle according to claim 2, wherein the positioning stopper of the core rod is arranged at a bottom of the rotary positioning block, and after the rear end of the core rod passes through the central hole of the rotary positioning block, the rotation preventing convex step of the core rod is embedded in a positioning hole on the linear push block.

4. The lead puncture needle according to claim 1, wherein the core rod or/and the puncture needle is/are in special geometric shapes conforming to clinical requirements, at least including a linear shape, an arc shape, an L shape, a C shape, a U shape, an S shape, and the like.

5. The lead puncture needle according to claim 1, wherein the lead slot is a bidirectional lead slot, and the lead slot is configured to pull the surgical suture into tissue or pull the surgical suture out of the tissue.

6. The lead puncture needle according to claim 1, wherein the puncture needle comprises a mounting convex step, and a puncture needle mounting slot is arranged in the mounting slot; and the puncture needle is mounted in the puncture needle mounting slot on the shell by the mounting convex step.

7. The lead puncture needle according to claim 6, wherein the mounting convex step and the puncture needle mounting slot are connected together by concave-convex clamp fit, screw connection, interference fit or bonding.

8. The lead puncture needle according to claim 6, wherein the mounting convex step comprises a connecting end and a limiting end, the connecting end comprises a connecting rod, and the limiting end comprises a connecting rod mounting hole and a limiting convex step; the puncture needle mounting slot is provided with a limiting slot; and the connecting rod is mounted in the connecting rod mounting hole, and the limiting convex step of the limiting end is mounted in the limiting slot, that is, the puncture needle is mounted in the puncture needle mounting slot.

9. The lead puncture needle according to claim 1, wherein the puncture safety protection mechanism is an automatic protection mechanism or a manual protection mechanism.

10. The lead puncture needle according to claim 9, wherein the puncture safety protection mechanism is an automatic protection mechanism.

11. The lead puncture needle according to claim 10, wherein the puncture safety protection mechanism comprises a safety spring, a safety spring rear positioning member and a safety spring front positioning member; the safety spring is mounted between the safety spring rear positioning member and the safety spring front positioning member; when the safety spring is compressed, the sharp tip of the puncture needle is exposed to perform puncture; after the puncture is completed, under an elastic force of the safety spring, the blunt head at a far end of the core rod protrudes out of the sharp tip of the puncture needle for safety protection and avoidance of accidental injury to normal tissue.

12. The lead puncture needle according to claim 1, wherein the stroke control convex step is arranged on an inner wall of the stroke control member.

13. The lead puncture needle according to claim 1, wherein a limiting convex step is arranged on the linear push block.

14. The lead puncture needle according to claim 1, wherein the linear push block and the button are integrated into one piece.

15. The lead puncture needle according to claim 1, wherein the linear push block and the button are connected together by concave-convex clamp fit, screw connection, interference fit, or bonding.

16. The lead puncture needle according to claim 1, wherein the shell is provided with a press block and a sealing member; the core rod passes through a central hole of the press block and a central hole of the sealing member; the press block presses the sealing member; and the sealing member forms dynamic seal for the core rod.

17. The lead puncture needle according to claim 1, wherein the shell is provided with a gas/water inlet.

18. The lead puncture needle according to claim 1, wherein the shell is provided with an observation scale.

19. The lead puncture needle according to claim 1, wherein the lead puncture needle is made of a medical material.

20. The lead puncture needle according to claim 1, wherein the core rod and the puncture needle are made of a medical shape memory alloy.

* * * * *